United States Patent
Goutsis et al.

(10) Patent No.: US 10,285,917 B2
(45) Date of Patent: May 14, 2019

(54) SOLID-STABILIZED COLORING CREAMS AND KIT FOR DYEING HAIR

(71) Applicant: Henkel AG & Co. KGaA, Duesseldorf (DE)

(72) Inventors: Konstantin Goutsis, Juechen (DE); Bernd Anderheggen, Moenchengladbach (DE)

(73) Assignee: Henkel AG & Co. KGaA (DE)

(*) Notice: Subject to any disclaimer, the term of this patent is extended or adjusted under 35 U.S.C. 154(b) by 0 days.

(21) Appl. No.: 15/584,824

(22) Filed: May 2, 2017

(65) Prior Publication Data

US 2017/0319441 A1 Nov. 9, 2017

(30) Foreign Application Priority Data

May 3, 2016 (DE) .................. 10 2016 207 569

(51) Int. Cl.

| | |
|---|---|
| *A61Q 5/10* | (2006.01) |
| *A61K 8/06* | (2006.01) |
| *A61K 8/19* | (2006.01) |
| *A61K 8/22* | (2006.01) |
| *A61K 8/30* | (2006.01) |
| *A61K 8/36* | (2006.01) |
| *A61K 8/34* | (2006.01) |
| *A61K 8/73* | (2006.01) |
| *A61K 8/02* | (2006.01) |

(52) U.S. Cl.
CPC ............ *A61K 8/062* (2013.01); *A61K 8/0241* (2013.01); *A61K 8/19* (2013.01); *A61K 8/22* (2013.01); *A61K 8/30* (2013.01); *A61K 8/342* (2013.01); *A61K 8/361* (2013.01); *A61K 8/732* (2013.01); *A61Q 5/10* (2013.01); *A61K 2800/412* (2013.01); *A61K 2800/4324* (2013.01); *A61K 2800/882* (2013.01)

(58) Field of Classification Search
CPC ... A61Q 5/10; A61K 8/19; A61K 8/22; A61K 8/361; A61K 8/30
See application file for complete search history.

(56) References Cited

U.S. PATENT DOCUMENTS

| | | |
|---|---|---|
| 3,920,883 A | 11/1975 | Yamada et al. |
| 4,767,741 A | 8/1988 | Komor et al. |
| 4,931,218 A | 6/1990 | Schenker et al. |
| 2002/0054890 A1 | 5/2002 | Gers-Barlag et al. |
| 2010/0175202 A1 | 7/2010 | Simonet et al. |
| 2013/0048008 A1 | 2/2013 | Iizaki |
| 2015/0297481 A1* | 10/2015 | Wahler ............ A61K 8/29 424/401 |
| 2016/0074292 A1 | 3/2016 | Goutsis et al. |

FOREIGN PATENT DOCUMENTS

| | | |
|---|---|---|
| DE | 19827434 A1 | 12/1999 |
| WO | 2013152956 A1 | 10/2013 |

OTHER PUBLICATIONS

UKIPO Combined Search and Examination Report GB1706924.6 Completed: Jan. 24, 2018; dated Jan. 25, 2018 6 pages.

* cited by examiner

Primary Examiner — Eisa B Elhilo
(74) Attorney, Agent, or Firm — James J. Cummings

(57) ABSTRACT

A dyeing agent (A) for dyeing keratinic fibers, in particular human hair, which is present in the form of an oil-in-water emulsion (O/W emulsion), includes
 (a1) an oil phase, including one or more fatty components (F),
 (a2) an aqueous phase,
 (a3) at least one oxidation dye precursor (ODP) and/or at least one direct dye (D), and
 (a4) at least one type of finely divided particles (P) that have an average particle size of less than 200 μm.
A multi-component packaging unit includes the aforementioned dyeing agent (A) and a separately packaged oxidizing agent preparation (B).

17 Claims, No Drawings

SOLID-STABILIZED COLORING CREAMS AND KIT FOR DYEING HAIR

FIELD OF THE INVENTION

The present invention is related to a dyeing agent (A) for dyeing keratinic fibers, which is present in the form of an oil-in-water emulsion (O/W emulsion) and includes an oil phase, an aqueous phase, dyes, and at least one type of finely divided particles (P). The present invention also relates to a multi-component packaging unit in which the aforementioned dyeing agent (A) is present separately packaged, in addition to an oxidizing agent preparation (B), and to a method for producing the dyeing agent (A).

BACKGROUND OF THE INVENTION

The use of emulsions is widespread in cosmetics. An emulsion is understood to be a finely distributed mixture of two normally immiscible liquids without visible separation.

A finely distributed mixture of two liquids, such as, for example, oil and water, is present in an emulsion. In this case, one of the liquids (phase) forms small drops, which are present distributed in the other liquid (phase). The phase forming the droplets is called the internal phase or also the dispersed phase. The phase in which the droplets float is called the external phase or also the continuous phase.

Emulsions belong to dispersed systems and differ from mixtures of miscible liquids. Emulsions are usually cloudy, milky liquids. In the case of emulsions comprising an aqueous phase and an oil phase, oil-in-water emulsions (O/W emulsions) and water-in-oil emulsions (W/O emulsions) are differentiated.

Emulsions are thermodynamically unstable. The dispersed (internal) phase strives to combine by coalescence to form larger areas and in so doing, the interfacial energy between the two phases is reduced. Emulsions used in cosmetics, however, should be preserved usually for a specific time period (between a few hours and a few years) and under certain conditions (e.g., within certain temperature and pH value ranges).

An emulsifier, i.e., a surfactant or a surface-active compound, which facilitates the formation of droplets and counteracts separation (phase separation), is therefore normally used to stabilize the emulsion. Emulsifiers reduce the interfacial tension between the phases by forming interfacial films at the phase boundary between oil and water, as a result of which the irreversible flowing together of the droplets (coalescence) is counteracted. Cloudy emulsions with a droplet size in the micrometer range normally form.

An emulsion can also be stabilized by the addition of specific solids. Solid-stabilized emulsions are often called Pickering emulsions after their discoverer. In 1907, S.U. Pickering demonstrated that small particles that are wetted better by water than by oil can stabilize O/W emulsions. It is important for the sufficient stabilization that a mechanically stable solid film can form around the dispersed phase.

A cosmetic Pickering emulsion can be, for example, an emulsion stabilized by colloidal silica particles. These silica particles arrange themselves at the interface between the two phases (hydrophilic and lipophilic phase) and prevent the droplets of the dispersed internal phase from coalescing (joining of the droplets).

To stabilize the emulsion, Pickering emulsions or solid-stabilized emulsions include particulate solids; said solids can be used either instead of surfactants or also in addition to surfactants. An essential advantage of solid-stabilized emulsions is that the surfactant concentration in the emulsion can be greatly reduced. After reduction of the surfactant concentration as well, solid-stabilized emulsions or Pickering emulsions are generally notable for a very good long-term stability.

A further advantage of Pickering emulsions is their high stability to changes in the chemical milieu such as, for example, a change in the pH values or salt concentrations.

The principle of stabilizing cosmetic emulsions by using particulate solids is already known from the prior art. For example, Pickering emulsions are described in EP 0987002, which are characterized by an oil phase, an aqueous phase, and at least one type of microfine particles with an average particle size of less than 200 nm. The emulsions in EP 0987002 are to be suitable for use as a cleansing emulsion, as a facial or body care preparation, as a sunscreen, or as a deodorant, and in particular have an improved skin tolerance.

Finely divided W/O emulsions with oil droplets in the micrometer range, which are free of surfactants and are stabilized by solids alone, are described in EP 0686391. For stabilization in this case, spherical polyalkylsilsesquioxane particles are employed which have a diameter of 100 nm up to 20 μm. Finely divided O/W emulsions with oil droplets in the micrometer range are described in EP 870495; here, apart from finely divided solids with a diameter of up to 200 nm, surfactants are also used as emulsifiers.

Surfactant-free droplet O/W macroemulsions with an oil droplet particle diameter in the range of 0.1 millimeters to several centimeters, in which finely divided solid particles are also used as an emulsifier, are disclosed in U.S. Pat. No. 3,920,883 and U.S. Pat. No. 4,767,741.

All aforementioned documents describe emulsions that are packaged as a one-component product; i.e., the particular emulsion, whether used as a skin cream, sunscreen, cleansing agent, or as a deodorant as well, is used immediately after removal from the container in which it is provided.

The use of solid-stabilized emulsions is not known so far in cosmetic products the use of which requires prior mixing of two or more separately packaged preparations.

Hair dyes, in particular oxidative hair dyes, are a known example of cosmetic products in which the user must first prepare a ready-to-use mixture shortly before use by mixing various preparations.

Oxidative hair dyes customarily include oxidation dye precursors, so-called developer components and coupler components. The developer components form the actual dyes under the influence of oxidizing agents or atmospheric oxygen with one another or during coupling with one or more coupler components.

If the oxidative dyeing agent includes both oxidation dye precursors and oxidizing agents (such as, for example, hydrogen peroxide), thus both substance classes are packaged expediently separately from one another, so as to prevent a premature, undesirable reaction with one another, and are brought into contact with one another only immediately before use.

In order to prepare a ready-to-use oxidative dyeing agent, the user must therefore mix the first preparation, which includes color-imparting substances (i.e., the oxidation dye precursors and/or the direct dyes) with the second preparation which includes the oxidizing agent.

Generally, both dyeing agent (A) (which includes the oxidation dye precursors and/or the direct dyes) and oxidizing agent preparation (B) are emulsions. In this case, the viscosity of each emulsion must be selected so that both emulsions are thin enough, on the one hand, to assure a complete and homogeneous mixing but, on the other hand, they are adjusted to be sufficiently thick to prevent the dripping of the finished application mixture.

Both dyeing agent (A) and oxidizing agent preparation (B) are therefore optimally adjusted to a precisely defined viscosity range. The mixing of two relatively viscous preparations often poses problems for the user, because mixing of the two preparations becomes the more difficult and more time-consuming, the thicker or more viscous the two preparations are. In particular, if two preparations are to be shaken together, it often occurs that the user ends the mixing or shaking before the application mixture is completely homogeneous. If this nonhomogeneous application mixture is then applied to hair, the outcome is a "variegated" coloring result. When hair is dyed in dark shades, i.e., if especially high amounts of dyes are present in the application mixture, in the case of incomplete mixing an overall too weak color intensity can also result.

Accordingly, it is desirable to provide new dyeing agents for dyeing keratinic fibers that are present in emulsion form, are stable, and have an especially good tolerance to high dye contents. These dyeing agents should be capable of being mixed especially readily and rapidly with a second oxidizing agent preparation, so that after mixing a homogeneous application mixture in the optimally adjusted viscosity range forms. Moreover, the viscosities of the dyeing agent and the finished application mixture should be within the desired specification range after a rather long storage time as well; i.e., the viscosities of dyeing agents and the application mixture should not change or shift in an unforeseeable manner also after weeks of storage of the dyeing agent. Furthermore, other desirable features and characteristics of the present invention will become apparent from the subsequent detailed description of the invention and the appended claims, taken in conjunction with this background of the invention.

BRIEF SUMMARY OF THE INVENTION

A first subject of the present invention is a dyeing agent (A) for dyeing keratinic fibers, in particular human hair, which is present in the form of an oil-in-water emulsion (O/W emulsion), comprising
(a1) an oil phase, including one or more fatty components (F),
(a2) an aqueous phase,
(a3) at least one oxidation dye precursor (ODP) and/or at least one direct dye (D),
(a4) at least one type of finely divided particles (P) that have an average particle size of less than 200 µm (micrometers).

It emerged that dyeing agents (A) of the invention of this type are especially storage stable. Especially high amounts of charged dyes can be used in dyeing agents (A), without separation of the emulsion occurring. The viscosity could be adjusted to a specific range by using the finely divided particles (P) and kept within this range in a reliable manner after prolonged storage as well.

Furthermore, the oxidation dye precursors or direct dyes could be distributed very well and especially homogeneously in dyeing agents (A) of the invention, primarily if the dyes were used in salt form and/or were included in especially high amounts in dyeing agent (A). This homogeneous distribution was also retained after the application mixture was prepared, so that an especially uniform coloring result could be observed on the dyed hair as well.

Dyeing agents (A) of the invention are very particularly suitable, if they are used as a coloring cream in an oxidative dyeing agent. Suitable oxidative dyeing agents are characterized in that they are prepared before use by mixing at least two preparations, wherein the at least two preparations are provided in at least two separately packaged containers, and wherein one container (I) contains dyeing agent (A) and a further container (II) contains an oxidizing agent preparation (B). Oxidizing agent preparation (B) includes hydrogen peroxide as the oxidizing agent.

A second subject of the present invention is a multi-component packaging unit (kit of parts) for the oxidative dyeing of keratinic fibers, in particular human hair, comprising, packaged separately from one another,
a container (I) containing a cosmetic agent (A) and
a container (II) containing a cosmetic agent (B), wherein
agent (A) in container (I) is a dyeing agent (A) of the first subject of the invention and
agent (B) in container (II) is an oxidizing agent preparation (B), including hydrogen peroxide.

In other words, a second subject of the present invention is a multi-component packaging unit (kit of parts) for the oxidative dyeing of keratinic fibers, in particular human hair, comprising, packaged separately from one another,
a container (I) containing a cosmetic agent (A) and
a container (II) containing a cosmetic agent (B),
wherein
agent (A) in container (I) is a dyeing agent (A), which is present in the form of an oil-in-water emulsion (O/W emulsion), comprising
(a1) an oil phase, including one or more fatty components (F),
(a2) an aqueous phase,
(a3) at least one oxidation dye precursor (ODP) and/or at least one direct dye (D),
(a4) at least one type of finely divided particles (P) that have an average particle size of less than 200 µm (micrometers), and
agent (B) in container (II) is an oxidizing agent preparation (B), including hydrogen peroxide.

Dyeing agent (A) is mixed with oxidizing agent preparation (B) shortly before use. For mixing, for example, oxidizing agent preparation (B) can be transferred from container (II), in which it is packaged, to container (I), dyeing agent (A) already being found in container (I). It is likewise possible to transfer dyeing agent (A) from container (I), in which it was packaged, to container (II), oxidizing agent preparation (B) already being found in container (II). The mixing can occur in both cases, for example, by shaking the two preparations.

Alternatively, it is likewise possible to transfer both dyeing agent (A) from container (I) and oxidizing agent preparation (B) from container (II) to a third container, in which both preparations are then shaken, stirred, or mixed in a different manner.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now emerged surprisingly that the aforementioned object is achieved in an excellent manner by a dyeing agent, which is present in the form of an (O/W) emulsion, comprises, apart from an oil phase with solid components and aqueous phase, an oxidation dye precursors and/or direct dyes, and which is characterized by the content of at least one type of finely divided particles with an average particle size of less than 200 μm (micrometers).

Container (I) and/or (II) can be, for example, a bottle, a tube, a box, or a sachet.

The amounts in which coloring cream (A) and oxidizing agent preparation (B) are mixed together can be selected depending on the hair length or color intensity. It is typical to mix together coloring cream (A) and oxidizing agent preparation (B) in a weight ratio of 1:5 to 5:1. For reasons of user convenience, preferably a mixing ratio of 1:3 to 3:1, preferably of 2:1 to 2:1, and very particularly preferably of about 1:1 is selected. In the case of a mixing ratio of 2:1, the user mixes, for example, 200 g of coloring cream (A) and 100 g of oxidizing agent preparation (B).

Solid-stabilized emulsion

In a Pickering emulsion or solid-stabilized emulsion, the phenomenon is used that very finely divided solid particles have an additional stabilizing effect in emulsions. In this case, an accumulation of the solid substance at the phase boundary between oil/fat and water occurs in the form of a layer as a result of which the coalescence of the dispersed phases is prevented. A characteristic of the Pickering emulsion or solid-stabilized emulsion therefore is that the solid particles are arranged at the interface between the oil phase and the aqueous phase and there form a mechanical barrier against the coalescence of the droplets.

Preferably, at least part of the finely divided, powdered solid, included in dyeing agent (A) of the invention, is adsorbed at the phase interface between the oil phase and the aqueous phase and thereby exerts an emulsion-stabilizing effect. Preferably, the major part, in other words, more than 50%, particularly preferably of the entire finely divided, powdered solid is adsorbed between the first and second phase.

In a preferred embodiment, dyeing agent (A) of the invention is characterized in that in dyeing agent (A)

(a4) at least 10% by weight, preferably at least 30% by weight, more preferably at least 50% by weight, and very particularly preferably at least 70% by weight of the employed finely divided particles (P) are located at the interface between the oil phase and aqueous phase.

In a preferred embodiment, the multi-component packaging unit of the invention is characterized in that in dyeing agent (A)

(a4) at least 10% by weight, preferably at least 30% by weight, more preferably at least 50% by weight, and very particularly preferably at least 70% by weight of the employed finely divided particles (P) are located at the interface between the oil phase and aqueous phase.

Keratinic fibers

Dyeing agent (A) is an agent for dyeing keratinic fibers, in particular human hair. The multi-component packaging unit of the invention (kit of parts) is used for the oxidative dyeing of keratinic fibers, in particular human hair.

Keratinic fibers are understood to be wool, pelts, feathers, and particularly human hair. The agents of the invention for the oxidative changing of color can also be used in principle for coloring other natural fibers, however, such as, e.g., cotton, jute, sisal, linen, or silk, modified natural fibers such as, for example, regenerated cellulose, nitrocellulose, alkyl or hydroxyalkyl cellulose, or acetyl cellulose.

Dyeing agent (A)

Dyeing agent (A) is present in the form of an (O/W) emulsion. It is characterized according to the invention in that it comprises components (a1) and (a2) and (a3) and (a4) essential to the invention.

Oil phase and fatty components

Dyeing agent (A) of the invention comprises an oil phase (a1), which includes one or more fatty components (F). In other words, the oil phase is formed by the fatty component(s) (F). Alternatively, oil phase (a1) can also be called a fat phase or lipophilic phase. Still further lipophilic components (e.g., hydrophobic dyes or other hydrophobic formulation components) can also be present moreover in the oil or fat phase.

Fatty components (F) in the context of the invention are understood to be organic compounds with a solubility in water at room temperature (22° C.) and atmospheric pressure (760 mm Hg) of less than 1% by weight, preferably of less than 0.1% by weight. The definition of fatty components includes explicitly only uncharged (i.e., nonionic) compounds. Fatty components have at least one saturated or unsaturated alkyl group having at least 8 C atoms. The molar weight of the fatty components is a maximum of 5000 g/mol, preferably a maximum of 2500 g/mol, and particularly preferably a maximum of 1000 g/mol. The fatty components are neither polyoxyalkylated nor polyglycerylated compounds.

Preferred fatty components in this regard are understood to be components from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, and/or hydrocarbons. Only nonionic substances are regarded explicitly as fatty components in the context of the present invention. Charged compounds such as, for example, fatty acids and salts thereof are not understood to be a fatty component.

$C_{12}$-$C_{30}$ fatty alcohols can be saturated, mono- or polyunsaturated, linear or branched fatty alcohols having 12 to 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachidyl alcohol (eicosan-1-ol), heneicosyl alcohol (heneicosan-1-ol), and/or behenyl alcohol (docosan-1-ol).

Preferred linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidonyl alcohol ((5Z,8Z,11Z,14Z)-eicosa-5,8,11,14-tetraen-1-ol), erucyl alcohol ((13Z)-docos-13-en-1-ol), and/or brassidyl alcohol ((13E)-docosen-1-ol).

Preferred representatives of branched fatty alcohols are 2-octyldodecanol, 2-hexyldodecanol, and/or 2-butyldodecanol.

A $C_{12}$-$C_{30}$ fatty acid triglyceride in the context of the present invention is understood to be the triester of the trihydric alcohol, glycerol, with three equivalents of fatty acids. In this regard, both structurally similar and also different fatty acids can be involved in ester formations within a triglyceride molecule.

Fatty acids according to the invention are understood to be saturated or unsaturated, unbranched or branched, unsubstituted or substituted $C_{12}$-$C_{30}$ carboxylic acids. Unsaturated fatty acids can be mono- or polyunsaturated. In the case of an unsaturated fatty acid, the C—C double bond(s) thereof can have the cis or trans configuration.

Notable for particular suitability are fatty acid triglycerides in which at least one of the ester groups is formed from glycerol with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid], and/or nervonic acid [(15Z)-tetracos-15-enoic acid].

The fatty acid triglycerides can also be of natural origin. The fatty acid triglycerides, occurring in soybean oil, peanut oil, olive oil, sunflower oil, macadamia nut oil, Moringa oil, apricot kernel oil, Marula oil, and/or optionally hydrogenated castor oil, or mixtures thereof are especially suitable for use in the product of the invention.

A $C_{12}$-$C_{30}$ fatty acid monoglyceride is understood to be the monoester of the trihydric alcohol, glycerol, with a fatty acid equivalent. In this case, either the middle hydroxy group of glycerol or the terminal hydroxy group of glycerol can be esterified with the fatty acid.

Notable for particular suitability are $C_{12}$-$C_{30}$ fatty acid monoglycerides in which a hydroxy group of glycerol is esterified with a fatty acid, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid], or nervonic acid [(15Z)-tetracos-15-enoic acid].

A $C_{12}$-$C_{30}$ fatty acid diglyceride is understood to be the diester of the trihydric alcohol, glycerol, with two fatty acid equivalents. In this case, either the middle and one terminal hydroxy group of glycerol can be esterified with two fatty acid equivalents, or however both terminal hydroxy groups of glycerol are each esterified with one fatty acid. Glycerol can be esterified hereby both with two structurally similar and with two different fatty acids.

Notable for particular suitability are fatty acid diglycerides in which at least one of the ester groups is formed from glycerol with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid], and/or nervonic acid [(15Z)-tetracos-15-enoic acid].

Hydrocarbons are compounds consisting exclusively of carbon and hydrogen atoms and having 8 to 80 C atoms. Preferred in this regard are particularly aliphatic hydrocarbons such as, for example, mineral oils, liquid paraffin oils (e.g., liquid paraffin or light liquid paraffin), isoparaffin oils, semisolid paraffin oils, paraffin waxes, hard paraffin (solid paraffin), Vaseline, and polydecene.

Liquid paraffin oils (liquid paraffin and light liquid paraffin) have proven to be especially suitable in this regard. The hydrocarbon is very especially preferably liquid paraffin, also called white oil. Liquid paraffin is a mixture of purified, saturated, aliphatic hydrocarbons, which consists for the most part of hydrocarbon chains with a C-chain distribution of 25 to 35 C atoms.

In a particularly preferred embodiment, a dyeing agent (A) of the invention is characterized in that dyeing agent (A) includes one or more fatty components (F) from the group comprising $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, and/or hydrocarbons, preferably $C_{12}$-$C_{30}$ fatty alcohols and/or hydrocarbons, particularly preferably $C_{12}$-$C_{30}$ fatty alcohols.

In a particularly preferred embodiment, a multi-component packaging unit of the invention is characterized in that dyeing agent (A) includes one or more fatty components (F) from the group comprising $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, and/or the hydrocarbons, preferably $C_{12}$-$C_{30}$ fatty alcohols and/or the hydrocarbons, particularly preferably $C_{12}$-$C_{30}$ fatty alcohols.

During the preparation of dyeing agent (A) of the invention, preferably first one or more fatty components are heated to a temperature above the melting point of the fatty components and mixed with the aqueous phase while stirring. Optionally, emulsifiers or surfactants can also be added. The dyes ((ODP) and/or (DD)) are then typically added to this preparation. After cooling, the finely divided particles (P) are then added. An oil-in-water emulsion is obtained in this manner, in which the fatty component(s) (F) represent(s) the internal or dispersed phase.

The viscosity of dyeing agent (A) can be modified by selecting the type and amount of the fatty components (F). Moreover, increasing the amount of fatty components, in particular if $C_{12}$-$C_{30}$ fatty alcohols are used, in the emulsion can also exert an additional stabilizing effect.

For this reason, dyeing agent (A) of the invention includes the fatty component(s) preferably in specific amount ranges. It is very particularly preferable, if dyeing agent (A), based on the total weight of dyeing agent (A), includes one or more fatty components (F) in a total amount of 0.5 to 25.0% by weight, preferably of 3.5 to 22.0% by weight, more preferably of 5.0 to 17.0% by weight, and particularly preferably of 7.5 to 12.5% by weight.

In a particularly preferred embodiment, a dyeing agent (A) of the invention is characterized in that dyeing agent (A), based on the total weight of dyeing agent (A), includes one or more fatty components (F) in a total amount of 0.5 to 25.0% by weight, preferably of 3.5 to 22.0% by weight, more preferably of 5.0 to 17.0% by weight, and particularly preferably of 7.5 to 12.5% by weight.

In a particularly preferred embodiment, a multi-component packaging unit of the invention is characterized in that dyeing agent (A), based on the total weight of dyeing agent (A), includes one or more fatty components (F) in a total amount of 0.5 to 25.0% by weight, preferably of 3.5 to 22.0% by weight, more preferably of 5.0 to 17.0% by weight, and particularly preferably of 7.5 to 12.5% by weight.

It is explicitly very particularly preferred, if dyeing agent (A) includes one or more $C_{12}$-$C_{30}$ fatty alcohols as fatty components.

In a very particularly preferred embodiment, a dyeing agent (A) of the invention is characterized in that dyeing agent (A), based on the total weight of dyeing agent (A), includes one or more fatty components (F) from the group comprising $C_{12}$-$C_{30}$ fatty alcohols in a total amount of 0.5 to 25.0% by weight, preferably of 3.5 to 22.0% by weight, more preferably of 5.0 to 17.0% by weight, and particularly preferably of 7.5 to 12.5% by weight.

In a very particularly preferred embodiment, a multi-component packaging unit of the invention is characterized in that dyeing agent (A), based on the total weight of dyeing agent (A), includes one or more fatty components (F) from the group comprising $C_{12}$-$C_{30}$ fatty alcohols in a total amount of 0.5 to 25.0% by weight, preferably of 3.5 to 22.0% by weight, more preferably of 5.0 to 17.0% by weight and particularly preferably of 7.5 to 12.5% by weight.

Aqueous phase

In the dyeing agent of the invention, the aqueous phase (a2) is the external phase or also the continuous phase. The dyeing agent of the invention, based on the total weight of dyeing agent (A), preferably includes water in an amount of 50.0 to 90.0% by weight, preferably of 55.0 to 85.0% by weight, more preferably of 60.0 to 80.0% by weight, and particularly preferably of 65 to 75.0% by weight.

In a very particularly preferred embodiment, a dyeing agent (A) of the invention is characterized in that dyeing agent (A), based on the total weight of dyeing agent (A), includes water in an amount of 50.0 to 90.0% by weight, preferably of 55.0 to 85.0% by weight, more preferably of 60.0 to 80.0% by weight, and particularly preferably of 65 to 75.0% by weight.

In a very particularly preferred embodiment, a multi-component packaging unit of the invention is characterized in that dyeing agent (A), based on the total weight of dyeing agent (A), includes water in an amount of 50.0 to 90.0% by weight, preferably of 55.0 to 85.0% by weight, more preferably of 60.0 to 80.0% by weight, and particularly preferably of 65 to 75.0% by weight.

Oxidation dye precursor and/or direct dyes

Dyeing agent (A) includes at least one oxidation dye precursor (ODP) and/or at least one direct dye (D) as third feature (a3) essential to the invention.

Oxidation dye precursors can be divided into developers and couplers, wherein the developers because of their higher sensitivity to oxygen are used mostly in the form of their physiologically acceptable salts (e.g., in the form of their hydrochlorides, hydrobromides, hydrogen sulfates, or sulfates).

Coupler components during oxidative dyeing alone cause no significant coloring, but always require the presence of developer components. Because couplers are not as sensitive to oxygen as developers, they can in fact also be used in the form of their salts in the preparations, but are often also used in the free form (i.e., not in the salt form).

Preferred physiologically acceptable salts of developers are, for example, p-phenylenediamine×$H_2SO_4$, p-phenylenediamine×2 HCl, p-toluylenediamine×$H_2SO_4$, p-toluylenediamine×2 HCl, 2-(2-hydroxyethyl)-p-phenylenediamine×$H_2SO_4$, 2-(2-hydroxyethyl)-p-phenylenediamine×2 HCl, 2-(1,2-dihydroxyethyl)-p-phenylenediamine×$H_2SO_4$, 2-(1,2-dihydroxyethyl)-p-phenylenediamine×2 HCl, N,N-bis(2-hydroxyethyl)-p-phenylenediamine×$H_2SO_4$, N,N-bis(2-hydroxyethyl)-p-phenylenediamine×2 HCl, 2-methoxymethyl-p-phenylenediamine×$H_2SO_4$, 2-methoxymethyl-p-phenylenediamine×2 HCl, N-(4-amino-3-methylphenyl)-N-[3-(1H-imidazol-1-yl)propyl]amine×$H_2SO_4$, N-(4-amino-3-methylphenyl)-N-[3-(1H-imidazol-1-yl)propyl]amine×2 HCl, N-(4-Amino-3-methylphenyl)-N-[3-(1H-imidazol-1-yl)propyl]amine×3 HCl, bis(2-hydroxy-5-aminophenyl)methane×$H_2SO_4$, bis(2-hydroxy-5-aminophenyl)methane×2 HCl, 4,5-diamino-1-(2-hydroxyethyl)-1H-pyrazole×$H_2SO_4$, 4,5-diamino-1-(2-hydroxyethyl)-1H-pyrazole×2 HCl, 2,4,5,6-tetraaminopyrimidine×$H_2SO_4$, 2,4,5,6-tetraaminopyrimidine×$2H_2SO_4$, 2,4,5,6-tetraaminopyrimidine×2 HCl, 2,4,5,6-tetraaminopyrimidine×3 HCl, 2,4,5,6-tetraaminopyrimidine×4 HCl, 4-hydroxy-2,5,6-triaminopyrimidine×$H_2SO_4$, 4-hydroxy-2,5,6-triaminopyrimidine×2 HCl, 2-hydroxy-4,5,6-triaminopyrimidine×$H_2SO_4$, 2-hydroxy-4,5,6-triaminopyrimidine×2 HCl, and 2-hydroxy-4,5,6-triaminopyrimidine×3 HCl.

It emerged during the work leading to this invention that in particular shades with a high quantitative proportion of oxidation dye precursors, i.e., brown shades, black shades, or other dark shades, can be stabilized very well by the finely divided particles (P) of type (a4). This effect is the more pronounced, if the oxidation dye precursors are used in the form of their physiologically acceptable salts.

In a very particularly preferred embodiment, a dyeing agent (A) of the invention is characterized in that dyeing agent (A) includes (a3) at least one oxidation dye precursor (ODP) of the developer type, which is used in the form of its salt and is selected from the group comprising p-phenylenediamine×$H_2SO_4$, p-phenylenediamine×2 HCl, p-toluylenediamine×$H_2SO_4$, p-toluylene-diamine×2 HCl, 2-(2-hydroxyethyl)-p-phenylenediamine×$H_2SO_4$, 2-(2-hydroxyethyl)-p-phenylenediamine×2 HCl, 2-(1,2-dihydroxyethyl)-p-phenylene-diamine×$H_2SO_4$, 2-(1,2-dihydroxyethyl)-p-phenylenediamine×2 HCl, N,N-bis(2-hydroxyethyl)-p-phenylenediamine×$H_2SO_4$, N,N-bis(2-hydroxyethyl)-p-phenylenediamine×2 HCl, 2-methoxymethyl-p-phenylenediamine×$H_2SO_4$, 2-methoxymethyl-p-phenylenediamine×2 HCl, N-(4-amino-3-methylphenyl)-N-[3-(1H-imidazol-1-yl)propyl]amine×$H_2SO_4$, N-(4-amino-3-methylphenyl)-N-[3-(1H-imidazol-1-yl)propyl]amine×2 HCl, N-(4-Amino-3-methylphenyl)-N-[3-(1H-imidazol-1-yl)propyl]amine×3 HCl, bis(2-hydroxy-5-aminophenyl)methane×$H_2SO_4$, bis(2-hydroxy-5-aminophenyl)methane×2 HCl, 4,5-diamino-1-(2-hydroxyethyl)-1H-pyrazole×$H_2SO_4$, 4,5-diamino-1-(2-hydroxyethyl)-1H-pyrazole×2 HCl, 2,4,5,6-tetraaminopyrimidine×$H_2SO_4$, 2,4,5,6-tetraaminopyrimidine×$2H_2SO_4$, 2,4,5,6-tetraaminopyrimidine×2 HCl, 2,4,5,6-tetraaminopyrimidine×3 HCl, 2,4,5,6-tetraaminopyrimidine×4 HCl, 4-hydroxy-2,5,6-triaminopyrimidine×$H_2SO_4$, 4-hydroxy-2,5,6-triaminopyrimidine×2 HCl, 2-hydroxy-4, 5,6-triaminopyrimidine×$H_2SO_4$, 2-hydroxy-4,5,6-triaminopyrimidine×2 HCl, and 2-hydroxy-4,5,6-triaminopyrimidine×3 HCl.

In a very particularly preferred embodiment, a multi-component packaging unit of the invention is characterized in that dyeing agent (A) includes (a3) at least one oxidation dye precursor (ODP) of the developer type, which is used in the form of its salt and is selected from the group comprising p-phenylenediamine×$H_2SO_4$, p-phenylenediamine×2 HCl, p-toluylenediamine×$H_2SO_4$, p-toluylene-diamine×2 HCl, 2-(2-hydroxyethyl)-p-phenylenediamine×$H_2SO_4$, 2-(2-hydroxyethyl)-p-phenylenediamine×2 HCl, 2-(1,2-dihydroxyethyl)-p-phenylene-diamine×$H_2SO_4$, 2-(1,2-dihydroxyethyl)-p-phenylenediamine×2 HCl, N,N-bis(2-hydroxyethyl)-p-phenylenediamine×$H_2SO_4$, N,N-bis(2-hydroxyethyl)-p-phenylenediamine×2 HCl, 2-methoxymethyl-p-phenylenediamine×$H_2SO_4$, 2-methoxymethyl-p-phenylenediamine×2 HCl, N-(4-amino-3-methylphenyl)-N-[3-(1H-imidazol-1-yl)propyl]amine×$H_2SO_4$, N-(4-amino-3-methylphenyl)-N-[3-(1H-imidazol-1-yl)propyl]amine×2 HCl, N-(4-Amino-3-methylphenyl)-N-[3-(1H-imidazol-1-yl)propyl]amine×3 HCl, bis(2-hydroxy-5-aminophenyl)methane×$H_2SO_4$, bis(2-hydroxy-5-aminophenyl)methane×2 HCl, 4,5-diamino-1-(2-hydroxyethyl)-1H-pyrazole×$H_2SO_4$, 4,5-diamino-1-(2-hydroxyethyl)-1H-pyrazole×2 HCl, 2,4,5,6-tetraaminopyrimidine×$H_2SO_4$, 2,4,5,6-tetraaminopyrimidine×$2H_2SO_4$, 2,4,5,6-tetraaminopyrimidine×2 HCl, 2,4,5,6-tetraaminopyrimidine×3 HCl, 2,4,5,6-tetraaminopyrimidine×4 HCl, 4-hydroxy-2,5,6-triaminopyrimidine×$H_2SO_4$, 4-hydroxy-2,5,6-triaminopyrimidine×2 HCl, 2-hydroxy-4, 5,6-triaminopyrimidine×$H_2SO_4$, 2-hydroxy-4,5,6-triaminopyrimidine×2 HCl, and 2-hydroxy-4,5,6-triaminopyrimidine×3 HCl.

Depending on the desired coloring result, oxidation dye precursors of the developer and coupler type are employed in different quantitative proportions in the dyeing agent.

If dyeing to a blond shade is desired, thus the use of oxidation dye precursors in a total amount below 1.0% by weight or even below 0.5% by weight is usually sufficient.

If, however, the user desires dyeing in a very dark tint, for example, in a dark-brown shade or in a black shade, this therefore requires the use of oxidation dye precursors in a total amount of at least 2.0% by weight, often 3.0% by weight, and in especially dark shades (black) even above of 4.5% by weight (based on the total weight of dyeing agent (A)).

The higher the dye content, the more difficult it is to stabilize this emulsion. It has emerged in this regard that it is also possible to stabilize very well brown or black shades by the finely divided particles (P) of type (a4). Preferably, dyeing agent (F) therefore includes one or more oxidation dye precursors (ODP) in a total amount of 2.0 to 8.0% by weight, preferably of 3.0 to 8.0% by weight, more preferably of 3.5 to 8.0% by weight, even more preferably of 4.0 to 8.0% by weight, and very particularly preferably of 4.5 to 8.0% by weight. The indicated amount ranges indicate the total amount of all oxidation dye precursors (developer and coupler) which are included in dyeing agent (F) and are used in relation to the total weight of dyeing agent (A).

In a very particularly preferred embodiment, a dyeing agent (A) of the invention is characterized in that dyeing agent (A), based on the total weight of dyeing agent (A), includes
(a3) one or more oxidation dye precursors (ODP) in a total amount of 2.0 to 8.0% by weight, preferably of 3.0 to 8.0% by weight, more preferably of 3.5 to 8.0% by weight, even more preferably of 4.0 to 8.0% by weight, and very particularly preferably of 4.5 to 8.0% by weight.

In a very particularly preferred embodiment, a multi-component packaging unit of the invention is characterized in that dyeing agent (A), based on the total weight of dyeing agent (A), includes
(a3) one or more oxidation dye precursors (ODP) in a total amount of 2.0 to 8.0% by weight, preferably of 3.0 to 8.0% by weight, more preferably of 3.5 to 8.0% by weight, even more preferably of 4.0 to 8.0% by weight, and very particularly preferably of 4.5 to 8.0% by weight.

The agent of the invention can include oxidation dye precursors of the developer type as the sole color-changing compounds. It is preferred according to the invention, however, if dyeing agent (A) includes in addition at least one oxidation dye precursor of the coupler type (called a coupler for short).

Coupler components during oxidative dyeing alone cause no significant coloring, but always require the presence of developer components. Coupler components in the context of the invention permit at least one substitution of a chemical group of the coupler by the oxidized form of the developer component. In this regard, covalent bonds form between the coupler and developer component.

Preferably at least one compound from one of the following classes is selected as a coupler component suitable according to the invention:
m-aminophenol and/or derivatives thereof,
m-diaminobenzene and/or derivatives thereof,
o-diaminobenzene and/or derivatives thereof,
o-aminophenol derivatives such as for example, o-aminophenol,
naphthalene derivatives with at least one hydroxy group,
di- or trihydroxybenzene and/or derivatives thereof,
pyridine derivatives,
pyrimidine derivatives,
monohydroxyindole derivatives and/or monoaminoindole derivatives,
monohydroxyindoline derivatives and/or monoaminoindoline derivatives,
pyrazolone derivatives such as, for example, 1-phenyl-3-methylpyrazol-5-one,
morpholine derivatives such as, for example, 6-hydroxybenzomorpholine or 6-aminobenzomorpholine,
quinoxaline derivatives such as, for example, 6-methyl-1,2,3,4-tetrahydroquinoxaline.

Mixtures of two or more compounds from one or more of said classes are likewise inventive in the context of this embodiment.

In a further embodiment, a dyeing agent (F) of the invention is characterized in that it includes at least one oxidation dye precursor of the coupler type, which is selected from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4, 5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5- dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, and the physiologically acceptable salts thereof.

Dyeing agents (F) of the invention can include at least one direct dye (D) in addition to the oxidation dye precursors or instead of them. In this case, these are dyes that are directly absorbed onto the hair and do not require any oxidative process to develop the color. Direct dyes are usually nitrophenylenediamines, nitroaminophenols, azo dyes, anthraquinones, triarylmethane dyes, or indophenols.

Direct dyes can be divided into anionic, cationic, and nonionic direct dyes.

Nonionic nitro and quinone dyes and neutral azo dyes are particularly suitable as nonionic direct dyes. Preferred nonionic direct dyes are the compounds known under the international names or trade names: HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Anionic direct dyes carry at least one negative charge and are also called acid dyes in the literature. Preferred anionic direct dyes are the compounds known under the international names or trade names: bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Cationic dyes are characterized by the presence of at least one positive charge. Cationic dyes are also called "basic dyes" in the English-language literature. Preferred cationic direct dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31, and Basic Red 51.

The stabilization of emulsions is often the more difficult, the higher the salt content of an emulsion. Therefore, emulsions in which high amounts of cationic and/or anionic direct dyes are used, are also typically more difficult to stabilize than emulsions with a low dye content or emulsions that only include nonionic direct dyes.

It emerged during the executed work that dyeing agents (A) present in emulsion form in particular can also be stabilized very well, if dyeing agent (A) includes cationic direct dyes and/or anionic direct dyes.

In a very particularly preferred embodiment, a dyeing agent (A) of the invention is characterized in that dyeing agent (A) includes
(a3) at least one direct dye (D) that carries at least one cationic or at least one anionic charge.

In a very particularly preferred embodiment, a multi-component packaging unit of the invention is characterized in that dyeing agent (A) includes
(a3) at least one direct dye (D) that carries at least one cationic or at least one anionic charge.

In principle, dyeing agent (A) of the invention can include the direct dyes in a total amount of 0.001 to 10% by weight.

It emerged further, however, during the executed work that dyeing agent (A) present in emulsion form in particular can also be stabilized very well, if dyeing agent (A) includes very high total amounts of direct dyes. Thus, a dyeing agent of the invention that includes one or more direct dyes (D) in a total amount of 2.0 to 8.0% by weight, preferably of 3.0 to 8.0% by weight, more preferably of 3.5 to 8.0% by weight, even more preferably of 4.0 to 8.0% by weight, and very particularly preferably of 4.5 to 8.0% by weight also proved to be stable after weeks of storage at low temperatures. All direct dyes were still homogeneously distributed in the emulsion also after weeks of storage.

In a very particularly preferred embodiment, a dyeing agent (A) of the invention is characterized further in that dyeing agent (A), based on the total weight of dyeing agent (A), includes
(a3) one or more direct dyes (D) in a total amount of 2.0 to 8.0% by weight, preferably of 3.0 to 8.0% by weight, more preferably of 3.5 to 8.0% by weight, even more preferably of 4.0 to 8.0% by weight, and very particularly preferably of 4.5 to 8.0% by weight.

In a very particularly preferred embodiment, a multi-component packaging unit of the invention is characterized further in that dyeing agent (A), based on the total weight of dyeing agent (A), includes
(a3) one or more direct dyes (D) in a total amount of 2.0 to 8.0% by weight, preferably of 3.0 to 8.0% by weight, more preferably of 3.5 to 8.0% by weight, even more preferably of 4.0 to 8.0% by weight, and very particularly preferably of 4.5 to 8.0% by weight.

Finely divided particles

A fourth component, essential to the invention, of dyeing agent (A) of the invention and the multi-component packaging unit of the invention is their content of (a4) at least one type of finely divided particles (P) that have an average particle size of less than 200 μm (micrometers).

A type of particles is understood to mean a plurality of small particles of a specific solid type. Overall the totality of the particles of the particular type of solid results in a pourable powder, consisting of particles on one type.

Dyeing agent (A) of the invention or dyeing agent (A) in the multi-component packaging unit of the invention can include particles of one type. In this case, all particles consist of the same solid material. If dyeing agent (A) of the invention or dyeing agent (A) in the multi-component packaging unit of the invention includes different types of particles, then the particles consist of different solids; i.e., the particles present in dyeing agent (A) differ with respect to their material.

Finely divided in the context of the present invention means that the particles of the particular type are small and have an average particle size of less than 200 μm (micrometers).

Particle size in the context of the present invention is understood to mean the average particle size. Laser diffractometry, for example, which alternatively is also called light diffraction analysis, can be used to determine the particle size.

The average particle size in the context of the present invention is particle sizes measured by laser diffractometry.

Laser (Light Amplification by Stimulated Emission of Radiation) means light amplification by stimulated emission. The photons emitted in the stimulated emission all have the same wavelength, so that laser light is always monochromatic and simultaneously much more intense than light from a conventional light source. A helium-neon laser with a wavelength of 632.8 nm is preferably used for the laser diffractometer.

Diffraction is generally described as the deflection of waves on an obstacle. After the particles are illuminated, a diffraction pattern with high wave peaks and narrow intervals (large particles) or small wave peaks with larger intervals (small particles) results depending on the particle size. The wave fronts are called Fraunhofer diffraction rings and the intervals between the wave fronts are called the diffraction angle. Laser diffractometry therefore utilizes the fact that the size of the diffraction angle is inversely proportional to the particle size.

A laser diffractometer consists of a light source (laser), a lens system, so as to widen the narrow laser beam, so that the entire sample can be illuminated, the measuring cell in which the sample is located, a Fourier lens, which bundles the beams, and a detector system. For example, a measuring instrument of the Mastersizer 2000 type from the company Malvern, or LA-920 from the company Horiba can be used for the laser diffractometry.

The detected diffraction patterns are then used for calculating the particle size by means of software and a PC. The particle sizes of the solid are calculated from the diffraction patterns. If there are different particle sizes in the solid, overlapping of the different diffraction patterns then results (interference).

The measuring results are normally presented as distribution curves, so that not only an indication of the average particle size but also information on the smallest and largest particles in the sample can be obtained.

D50 in this case indicates the average particle size. D50 means that 50% of the particles are smaller than the indicated value. Other important parameters are D10 as a measure for the smallest particles (10% of the particles are smaller than the indicated value) and D90, D95, D99, and D100 values as a measure for the largest particles (90%, 95%, 99%, or 100% of the particles are smaller than the indicated values). The closer D10 and D100 are, the narrower the particle size distribution.

The particle sizes can be given in principle as a volumetric diameter (D(v)) or as a numerical diameter (D(n)). If a volumetric diameter (D(v)) is provided, this means that the particle size refers to the volume of the particles. If a numerical diameter (D(n)) is provided, this means that the particle size refers to the number of particles.

The average particle size in the context of the present invention is understood to mean the average volumetric diameter (D(v)) of the particles.

In the case of spherical particles, the diameter corresponds to the diameter of the spherical particle. In the case of irregularly shaped particles, the diameter corresponds to the equivalent diameter of the particle. The equivalent diameter is understood to be the diameter of a sphere that has the same physical property as the measured, irregularly shaped particle in the determination of the particle feature.

An average particle size of less than 200 µm (micrometers) in the context of the present invention therefore means that D50(v) is equal to 200; i.e., 50% of the particles have a volumetric diameter of less than 200 µm (micrometers).

The finely divided particles (P) according to the invention are used in dyeing agent (A) in the form of finely divided, powdered solids. The solids can be both inorganic and organic powdered solids, and the particles can optionally also be coated and/or modified. The use of finely divided, powdered, optionally coated, and/or optionally modified solids from the group comprising starch, silicon dioxide, iron oxide, titanium oxide, magnesium oxide, aluminum oxide, zinc oxide, calcium aluminate, silicic acid, magnesium silicoaluminate, magnesium metasilicate aluminate, talc, mica, zirconium oxide, colloidal kaolin, bentonite, glass, zinc laurate, microcrystalline cellulose, mother-of-pearl, carbon black, calcium carbonate, and/or polyalkylsilsesquioxane has proven as especially suitable.

In a very particularly preferred embodiment, a dyeing agent (A) of the invention is characterized in that dyeing agent (A) includes (a4) at least one type of finely divided particles (P) which is selected from finely divided, powdered, optionally coated, and/or optionally modified solids from the group comprising starch, silicon dioxide, iron oxide, titanium oxide, magnesium oxide, aluminum oxide, zinc oxide, calcium aluminate, silicic acid, magnesium silicoaluminate, magnesium metasilicate aluminate, talc, mica, zirconium oxide, colloidal kaolin, bentonite, glass, zinc laurate, microcrystalline cellulose, mother-of-pearl, carbon black, calcium carbonate, and/or polyalkylsilsesquioxane.

In a very particularly preferred embodiment, a multi-component packaging unit of the invention is characterized in that dyeing agent (A) includes (a4) at least one type of finely divided particles (P) which is selected from finely divided, powdered, optionally coated, and/or optionally modified solids from the group comprising starch, silicon dioxide, iron oxide, titanium oxide, magnesium oxide, aluminum oxide, zinc oxide, calcium aluminate, silicic acid, magnesium silicoaluminate, magnesium metasilicate aluminate, talc, mica, zirconium oxide, colloidal kaolin, bentonite, glass, zinc laurate, microcrystalline cellulose, mother-of-pearl, carbon black, calcium carbonate, and/or polyalkylsilsesquioxane.

A particularly preferred type of finely divided particles (P) can be finely divided starch. Starch can be natural starch, starch of natural origin, coated starch, or also modified starch.

Used as naturals starch or starch of natural origin can be, for example, maize starch, rice starch, quinoa starch, corn starch, wheat starch, buckwheat starch, amaranth starch, cattail starch, potato starch, pea starch, acorn starch, chestnut starch, barley starch, wheat starch, banana starch, sago starch, millet starch, sorghum starch, oat starch, barley starch, rye starch, bean starch, sweet potato starch, arrowroot starch, or manioc starch.

The aforementioned starches can also be modified. Within the scope of the modification, the starches can be changed, for example, physically or chemically. Thus, the starches can be degraded oxidatively, for example, or carboxy-($C_1$-$C_4$)-alkyl groups can be introduced.

Starches that comprise at least one carboxy-($C_1$-$C_4$)-alkyl group are, for example, carboxymethyl starch, carboxyethyl starch, and carboxypropyl starch. Carboxymethyl starch is used, for example, in the form of the commercial product Covagel (carboxymethyl starch, sodium salt, potato starch being the starch source; INCI name: Sodium Carboxymethyl Starch) from the company Sensient/LCW.

The use of at least one type of finely divided particles (P) of hydrophobically modified starches has proven as very especially suitable.

Hydrophobically modified starches in the context of the present invention are understood to be starches whose polymer structure comprises at least one hydrophobic group, for example, one or more $C_8$-$C_{30}$ alkyl groups and/or $C_8$-$C_{30}$ alkenyl groups. These hydrophobic groups (e.g., the alkyl groups) can be present linked to the starch molecule, for example, via an ester group, an ether group, or an amide group.

A very particularly preferred hydrophobically modified starch is "aluminum starch octenylsuccinate," a starch modified with octenylsuccinic anhydride, which is present in the form of its aluminum salt.

Aluminum starch octenylsuccinate has the CAS no. 9087-61-0 and is commercially available, for example, under the trade name Covafluid AMD from the company Sensient.

A very particularly preferred aluminum starch octenylsuccinate has, for example, an average particle size (i.e., an average volumetric diameter (D(v)) of 10 to 20 µm (micrometers):

D10 (v)=9 µm (micrometers)
D50 (v)=16 µm (micrometers)
D90 (v)=23 µm (micrometers)

The type of finely divided particles (P) in a further very particularly preferred embodiment can also be finely divided silicon dioxide; the silicon dioxide can also be chemically or physically modified and/or coated or surface-treated.

For example, a coating of silicon dioxide with dimethylpolysiloxane is a mixture of completely methylated, linear siloxane polymers that are terminally capped with trimethylsilyloxy units is advantageous.

A coating of silicon dioxide with a mixture of dimethylpolysiloxane, in particular dimethylpolysiloxane with an average chain length of 200 to 350 dimethylsiloxane units, is advantageous.

The coating of silicon dioxide is also possible by reaction with a $C_1$-$C_4$ alkylslilane and/or a halogenated $C_1$-$C_4$ alkylsilane. $Me_3SiCl$, $Me_2SiCl_2$, or $MeSiCl_3$, for example, can be named as examples of halogenated $C_1$-$C_4$ alkylsilanes. The appropriately coated, finely divided silicon dioxide is commercially obtainable under the names Aerosil R 805, Aerosil R 812 and Aerosil R 974, and Aerosil R 972 from the company Evonik/Degussa.

Especially advantageous effects could be achieved, if at least one type of finely divided particles (P), which was selected from the finely divided, powdered, optionally coated, and/or optionally modified solids from the group of starch and/or silicon dioxide, was employed in dyeing agent (A).

In an explicitly very particularly preferred embodiment, a dyeing agent (A) of the invention is characterized in that dyeing agent (A) includes
(a4) at least one type of finely divided particles (P), which is selected from the finely divided, powdered, optionally coated, and/or optionally modified solids from the group of starch and/or silicon dioxide.

In an explicitly very particularly preferred embodiment, a multi-component packaging unit of the invention is characterized in that dyeing agent (A) includes
(a4) at least one type of finely divided particles (P), which is selected from the finely divided, powdered, optionally coated, and/or optionally modified solids from the group of starch and/or silicon dioxide.

The hydrophobically modified starches, in particular aluminum starch octenylsuccinate, are again selected very particularly preferably from the group of the optionally coated and/or optionally modified starches.

The hydrophobically modified silicon dioxides, in particular silica dimethyl silylate, are again selected very particularly preferably from the group of the optionally coated and/or optionally modified silicon dioxide.

Silica dimethyl silylate has the CAS no. 68611-44-9 and is the reaction product of silica with dichlorodimethylsilane ($Me_2SiCl_2$). The average particle size is 16 nm (nanometers), commercially marketed in the form of the raw material Aerosil R 972.

In an explicitly very particularly preferred embodiment, a dyeing agent (A) of the invention is characterized in that dyeing agent (A) includes
(a4) at least one type of finely divided particles (P), which is selected from finely divided, powdered aluminum starch octenylsuccinate and/or finely divided, powdered silica dimethyl silylate.

In an explicitly very particularly preferred embodiment, a multi-component packaging unit of the invention is characterized in that dyeing agent (A) includes
(a4) at least one type of finely divided particles (P), which is selected from finely divided, powdered aluminum starch octenylsuccinate and/or finely divided, powdered silica dimethyl silylate.

It was found that a variation of the amount used of the microfine particles (P) also influences the viscosity of dyeing agent (A). In order to adjust dyeing agent (A) to the viscosity range optimal for mixing with oxidizing agent preparation (B), the finely divided particles (P) are therefore used particularly preferably in specific amount ranges in dyeing agent (A). It emerged as especially advantageous in this regard to use one or more types of finely divided particles (P) in a total amount of 0.25 to 15.0% by weight, preferably of 1.0 to 10.0% by weight, more preferably of 1.5 to 5.0% by weight, and very particularly preferably of 1.8 to 3.2% by weight. In this case, the aforementioned quantitative data referred to the total amount of all finely divided particles (P), related to the total weight of dyeing agent (F).

Even if the finely divided particles were used in an amount of 0.25% by weight, the viscosity of dyeing agent (F) could be significantly increased. As a result of the increase in viscosity, higher amounts of dye ((ODP) and/or (D)) could be stored stably for a longer period of time. The viscosity of dyeing agent (F) could be increased still further selectively by a further increase in the particle amount (P).

It has emerged, furthermore, that the addition of the finely divided particles (P) also had a positive effect on the mixing viscosity of the finished application mixture. Even during mixing with a very thin oxidizing agent preparation (B), the viscosity of the application mixture could be kept in the desired viscosity range, without unforeseeable variations or storage-related changes occurring.

In an explicitly very particularly preferred embodiment, a dyeing agent (A) of the invention is characterized in that dyeing agent (A), based on the total weight of the dyeing agent (A), includes
(a4) one or more types of finely divided particles (P) in a total amount of 0.25 to 15.0% by weight, preferably of 1.0 to 10.0% by weight, more preferably of 1.5 to 5.0% by weight, and very particularly preferably of 1.8 to 3.2% by weight.

In an explicitly very particularly preferred embodiment, a multi-component packaging unit of the invention is characterized in that dyeing agent (A), based on the total weight of dyeing agent (A), includes
(a4) one or more types of finely divided particles (P) in a total amount of 0.25 to 15.0% by weight, preferably of 1.0 to 10.0% by weight, more preferably of 1.5 to 5.0% by weight, and very particularly preferably of 1.8 to 3.2% by weight.

The finely divided particles (P) according to the invention are characterized in that they have an average particle size of less than 200 µm (micrometers). It has emerged as especially advantageous in this regard to use particles that have an average particle size of 10 nm (nanometers) to 180 µm (micrometers), preferably of 10 nm (nanometers) to 140 µm (micrometers), more preferably of 10 nm (nanometers) to 80 µm (micrometers), and very particularly preferably of 10 nm (nanometers) to 40 µm (micrometers). In this regard, the form (platelets, rods, beads, etc.) of the employed particles is substantially immaterial.

In an explicitly very particularly preferred embodiment, a dyeing agent (A) of the invention is characterized in that dyeing agent (A) includes (a4) at least one type of finely divided particles (P) that have an average particle size of 10 nm (nanometers) to 180 µm (micrometers), preferably of 10 nm (nanometers) to 140 µm (micrometers), more preferably of 10 nm (nanometers) to 80 µm (micrometers), and very particularly preferably of 10 nm (nanometers) to 40 µm (micrometers).

In an explicitly very particularly preferred embodiment, a multi-component packaging unit of the invention is characterized in that dyeing agent (A) includes (a4) at least one type of finely divided particles (P) that have an average particle size of 10 nm (nanometers) to 180 µm (micrometers), preferably of 10 nm (nanometers) to 140 µm (micrometers), more preferably of 10 nm (nanometers) to 80 m (micrometers), and very particularly preferably of 10 nm (nanometers) to 40 µm (micrometers).

Furthermore, work leading to this invention has shown that it is possible to produce the viscosity of dyeing agent (A) solely by adding the fatty substances (F), by the dyes present in salt form, and by the finely divided particles (P). It is also possible therefore because of the use of the finely divided particles (P) to avoid the addition of thickening polymers.

Thickening polymers in the context of the present invention are synthetic polymers that are soluble in dyeing agent (A) or form a gel in dyeing agent (A). The thickening effect occurs due to solution or swelling (gel formation). Thickening polymers are thereby not meant to be explicitly substances that are present in dyeing agent (F) in the form of finely divided particles.

If a polymer is present as a type of finely divided particles with an average particle size of less than 200 µm (micrometers) and is not soluble or swellable in dyeing agent (A) (so that the polymer is retained in the form of finely divided particles in dyeing agent (A)), then this does not come under the definition of a thickening polymer in the context of the present invention.

For example, synthetic polymers that are soluble in dyeing agent (A) or swellable in dyeing agent (A) have a thickening effect and can be obtained by the polymerization of at least one unsaturated monomer need not be used. Suitable monomers are: (meth)acrylic acid, (meth)acrylic acid esters, (meth)acrylamide, ethylene, propylene, styrene, vinylpyrrolidone, or vinyl acetate, the aforementioned monomers also being able to carry other substituents.

In an explicitly very particularly preferred embodiment, a dyeing agent (A) of the invention is characterized in that dyeing agent (A) is substantially free of polymers that are obtained by polymerizing at least one monomer from the group comprising (meth)acrylic acid, (meth)acrylic acid esters, (meth)acrylamide, ethylene, propylene, styrene, vinylpyrrolidone, and vinyl acetate.

In an explicitly very particularly preferred embodiment, a multi-component packaging unit of the invention is characterized in that dyeing agent (A) is substantially free of polymers that are obtained by polymerizing at least one monomer from the group comprising (meth)acrylic acid, (meth)acrylic acid esters, (meth)acrylamide, ethylene, propylene, styrene, vinylpyrrolidone, and vinyl acetate.

The fact that dyeing agents (A) are substantially free of thickening polymers in this regard means that they do not include thickening polymers in amounts that would lead to thickening in dyeing agent (A). Substantially free of thickening polymers preferably means that dyeing agent (A), based on the total weight of dyeing agent (A), includes one or more thickening polymers in a total amount of at most 0.05% by weight, preferably at most 0.01% by weight, and very particularly preferably 0.001% by weight.

In an explicitly very particularly preferred embodiment, a dyeing agent (A) of the invention is characterized in that the total content in dyeing agent (A) of polymers that can be obtained by polymerizing at least one monomer from the group comprising (meth)acrylic acid, (meth)acrylic acid esters, (meth)acrylamide, ethylene, propylene, styrene, vinylpyrrolidone, and vinyl acetate is at most 0.05% by weight. In this case, the total content of polymers is based on the total weight of dyeing agent (A).

In an explicitly very particularly preferred embodiment, a multi-component packaging unit of the invention is characterized in that the total content in dyeing agent (A) of polymers that can be obtained by polymerizing at least one monomer from the group comprising (meth)acrylic acid, (meth)acrylic acid esters, (meth)acrylamide, ethylene, propylene, styrene, vinylpyrrolidone, and vinyl acetate is at most 0.05% by weight. In this case, the total content of polymers is based on the total weight of dyeing agent (A).

Polymers are understood to be macromolecules with a molecular weight of at least 1000 g/mol, preferably of at least 2500 g/mol, particularly preferably of at least 5000 g/mol, which consist of the same repeating organic units. Polymers are prepared by polymerization of a monomer type or by polymerization of various structurally different monomer types. If the polymer is prepared by the polymerization of one monomer type, the term homopolymers is used. If structurally different monomer types are used in the polymerization, the resulting polymer is called a copolymer.

The maximum molecular weight of the polymer depends on the degree of polymerization (number of polymerized monomers) and is also determined by the polymerization method. In the context of the present invention, it is preferred if the maximum molecular weight of the cationic polymer (d) is no more than $10^7$ g/mol, preferably no more than $10^6$ g/mol, and particularly preferably no more than $10^5$ g/mol.

To prepare the finished application mixture, dyeing agent (A) of the invention is mixed with an oxidizing agent preparation (B). The dyeing agent according to the invention is present in the form of an (O/W) emulsion, and the oxidizing agent preparation (B) is also preferably used in emulsion form, particularly preferably in the form of an (O/W) emulsion.

In order to assure an optimal and rapid mixability of preparations (A) and (B) as well, apart from good application technology properties, both preparation (A) and preparation (B) are preferably adjusted to a specific viscosity range.

The viscosity of dyeing agent (A) can be determined in particular by the interaction of the amount the fatty components (F) and the amount of finely divided particles (P).

Because very high dye amounts ((ODP) and/or (D)) need to be stabilized in some shades in dyeing agent (A), it emerged as advantageous if dyeing agent (F) is adjusted to a higher viscosity than oxidizing agent preparation (B).

Within this embodiment, for example, the thick or cream-like dyeing agent (A) can be present packaged in a tube. To mix (A) with (B), coloring cream (A) is then transferred from the tube to a bottle which already includes oxidizing agent preparation (B). Oxidizing agent preparation (B) is preferably thin. If both preparations (A) and (B) were adjusted to their optimal viscosity ranges, this assures a very rapid mixability and the production of a homogeneous, stable, and rheologically optimized application mixture. It is very particularly preferred for the aforementioned reasons, if dyeing agent (A) has a viscosity of 10,000 to 50,000 mPas, preferably of 10,000 to 40,000 mPas, and particularly preferably of 15,000 to 30,000 mPas (22° C./Brookfield viscometer/spindle 5/4 rpm).

In an explicitly very particularly preferred embodiment, a dyeing agent (A) of the invention is characterized in that dyeing agent (A) has a viscosity of 10,000 to 50,000 mPas, preferably of 10,000 to 40,000 mPas, and particularly preferably of 15,000 to 30,000 mPas (22° C./Brookfield viscometer/spindle 5/4 rpm).

In an explicitly very particularly preferred embodiment, a multi-component packaging unit of the invention is characterized in that dyeing agent (A) has a viscosity of 10,000 to 50,000 mPas, preferably of 10,000 to 40,000 mPas, and particularly preferably of 15,000 to 30,000 mPas (22° C./Brookfield viscometer/spindle 5/4 rpm).

Oxidizing agent preparation (B) is preferably adjusted to a thinner viscosity range. It is, for example, in the range of 1000 to 16,000 mPas, preferably of 2000 to 14,000 mPas, more preferably of 3000 to 12,000 mPas, and particularly preferably of 4000 to 10,000 mPas (22° C./Brookfield viscometer/spindle 5/4 rpm).

In an explicitly very particularly preferred embodiment, a multi-component packaging unit of the invention is characterized in that oxidizing agent preparation (B) has a viscosity of 1000 to 16,000 mPas, preferably of 2000 to 14,000 mPas, more preferably of 3000 to 12,000 mPas, and particularly preferably of 4000 to 10,000 mPas (22° C./Brookfield viscometer/spindle 5/4 rpm).

The application mixture prepared by mixing preparations (A) and (B) also preferably fulfills certain specification requirements in regard to its viscosity.

Dyeing agents (A) and (B) can be mixed together, for example, in a weight ratio of 1:5 to 5:1. Preferably a mixing ratio of 1:3 to 3:1, more preferably of 2:1 to 2:1, and very particularly preferably of about 1:1 is selected.

If, for example, a mixing ratio of 1:1 is selected (mixing of 100 g of dyeing agent (A) and 100 g of oxidizing agent preparation (B)), thus the viscosity is very particularly preferably in the range of 10,000 to 50,000 mPas, preferably of 12,000 to 45,000 mPas, more preferably of 12,000 to 40,000 mPas, and very particularly preferably of 12,000 to 35,000 mPas (22° C./Brookfield viscometer/spindle 5/4 rpm).

In an explicitly very particularly preferred embodiment, a multi-component packaging unit of the invention is characterized in that the mixture of dyeing agent (A) and oxidizing agent preparation (B), if (A) and (B) are mixed in a weight ratio of 1:1, has a viscosity of 10,000 to 50,000 mPas, preferably of 12,000 to 45,000 mPas, more preferably of 12,000 to 40,000 mPas, and very particularly preferably of 12,000 to 35,000 mPas (22° C./Brookfield viscometer/spindle 5/4 rpm).

Oxidizing agent preparation (B)

Oxidizing agent preparation (B) includes hydrogen peroxide as the oxidizing agent. Hydrogen peroxide can be used either as hydrogen peroxide itself or also in the form of its solid adducts to organic or inorganic compounds, such as urea, melamine, and sodium borate.

Preferably, the amount of oxidizing agents in oxidizing agent preparation (B), based on the total weight of oxidizing agent preparation (B), is 0.5 to 12% by weight, preferably 2 to 10% by weight, in particular preferably 3 to 6% by weight (calculated as 100% $H_2O_2$).

Such oxidizing agent preparations are preferably aqueous, flowable oxidizing agent preparations. In this case, preferred preparations are characterized in that the flowable oxidizing agent preparation, based on its weight, includes 40 to 90% by weight, preferably 50 to 85% by weight, particularly preferably 55 to 85% by weight, more preferably 60 to 85% by weight, and in particular 70 to 85% by weight of water.

It has proven advantageous, furthermore, if oxidizing agent preparation (B) includes at least one stabilizer or complexing agent. Common complexing agents and stabilizers that are preferred in the context of the present invention are, for example, polyoxycarboxylic acids, polyamines, ethylenediaminetetraacetic acid (EDTA), N-hydroxyethyl-ethylenediaminetriacetic acid, diethylenetriaminepentaacetic acid (DTPA), ethylenediaminedisuccinic acid (EDDS), hydroxyethyliminodiacetic acid, nitrilodiacetic acid-3-propionic acid, isoserinediacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylenediaminedisuccinic acid (HPDS), glycinamide-N,N'-disuccinic acid (GADS), ethylendiamine-N—N'-diglutaric acid (EDDG), 2-hydroxypropylenediamine-N—N'-disuccinic acid (HPDDS), diaminoalkyldi(sulfo succinic acid) (DDS), ethylenedicysteic acid (EDC), ethylenediamine-N—N'-bis(ortho-hydroxyphenyl)acetic acid (EDDHA), N-2-hydroxyethylamine-N,N-diacetic acid, glyceryl iminodiacetic acid, iminodiacetic acid-N-2-hydroxypropylsulfonic acid, aspartic acid-N-carboxymethyl-N-2,5-hydroxypropyl-3-sulfonic acid, 3-alanine-N,N'-diacetic acid, aspartic acid-N,N'-diacetic acid, aspartic acid-N-monoacetic acid, dipicolinic acid, and salts thereof and/or derivatives, geminal diphosphonic acid such as 1-hydroxyethane-1,1-diphosphonic acid (HEDP), the homologues thereof having up to 8 carbon atoms, and hydroxy or amino group-containing derivatives thereof and 1-aminoethane-1,1-diphosphonic acid, the higher homologues thereof having up to 8 carbon atoms, and hydroxy or amino group-containing derivatives, aminophosphonic acid such as ethylene diaminetetra(methylenephosphonic acid) (EDTMP), diethylenetriamine penta(methylenephosphonic acid) (DTPMP) and the higher homologues thereof, or nitrilotri(methylenephosphonic acid), phosphonopolycarboxylic acid such as 2-phosphonobutane-1,2,4-tricarboxylic acid, cyclodextrins, and alkali stannates (sodium stannate), alkali pyrophosphates (tetrasodium pyrophosphate, disodium pyrophosphate), alkali phosphates (sodium phosphate), and phosphoric acid and salts thereof.

Other ingredients

Dyeing agents (A) of the invention and/or oxidizing agent preparation (B) can also include in addition one or more surfactants.

Surfactants preferred according to the invention are selected from the group comprising anionic, cationic, amphoteric, and/or nonionic surfactants or mixtures thereof.

All anionic surface-active substances, suitable for use on the human body or on technical surfaces, are suitable as anionic surfactants in the compositions of the invention. These are characterized by an anionic group imparting water solubility, such as, e.g., a carboxylate, sulfate, sulfonate, or phosphate group, and a lipophilic alkyl group having approximately 8 to 30 C atoms. In addition, the molecule can include glycol ether or polyglycol ether groups, ester, ether, and amide groups, and hydroxyl groups. Examples of suitable foaming anionic surfactants are, each in the form of the sodium, potassium, and ammonium and mono-, di-, and trialkanolammonium salts having 2 to 4 carbon atoms in the alkanol group, acyl glutamates of the formula (I),

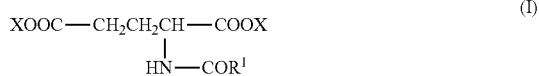

in which $R^1CO$ stands for a linear or branched acyl group having 6 to 22 carbon atoms and 0, 1, 2, or 3 double bonds and X for hydrogen, an alkali and/or alkaline earth metal, ammonium, alkyl ammonium, alkanol ammonium, or glucammonium, for example, acyl glutamates, derived from fatty acids having 6 to 22, preferably 12 to 18 carbon atoms, such as, for example, $C_{12/14}$ or $C_{12/18}$ coconut fatty acid, lauric acid, myristic acid, palmitic acid, and/or stearic acid, in particular sodium N-cocoyl- and sodium N-stearoyl-L-glutamate, esters of a hydroxy-substituted di- or tricarboxylic acid of the general formula (II),

in which X=H or is a —$CH_2COOR$ group, Y=H or is —OH on condition that Y=H, if X=—$CH_2COOR$, R, $R^1$, and $R^2$ independently of one another denote a hydrogen atom, an alkali or alkaline earth metal cation, an ammonium group, the cation of an ammonium-organic base or a group Z, which originates from a polyhydroxylated organic compound, selected from the group of etherified ($C_6$-$C_{18}$) alkyl polysaccharides with 1 to 6 monomeric saccharide units and/or etherified aliphatic ($C_6$-$C_{16}$) hydroxyalkylpolyols with 2 to 16 hydroxyl groups, with the proviso that at least one of the R, $R^1$, or $R^2$ groups is a Z group, esters of the sulfosuccinic acid salt of the general formula (III),

in which $R^1$ and $R^2$ independently of one another denote a hydrogen atom, an alkali or alkaline earth metal cation, an ammonium group, the cation of an ammonium-organic base or a group Z, which originates from a polyhydroxylated organic compound, selected from the group of etherified ($C_6$-$C_{18}$) alkyl polysaccharides with 1 to 6 monomeric saccharide units and/or etherified aliphatic ($C_6$-$C_{16}$) hydroxyalkylpolyols with 2 to 16 hydroxyl groups, with the proviso that at least one of the $R^1$ or $R^2$ groups is a Z group, sulfosuccinic acid mono- and -dialkyl esters having 8 to 24 C atoms in the alkyl group and sulfosuccinic acid monoalkyl polyoxyethyl esters having 8 to 24 C atoms in the alkyl group and 1 to 6 ethoxy groups, esters of tartaric acid and citric acid with alcohols, representing adducts of approximately 2 to 15 molecules of ethylene oxide and/or propylene oxide to fatty alcohols having 8 to 22 C atoms, linear and branched fatty acids having 8 to 30 C atoms (soaps), ether carboxylic acids of the formula R—O—($CH_2$—$CH_2O$)$_x$—$CH_2$—COOH, in which R is a linear alkyl group having 8 to 30 C atoms and x=0 or is 1 to 16, acyl sarcosinates with a linear or branched acyl group having 6 to 22 carbon atoms and 0, 1, 2, or 3 double bonds, acyl taurates with a linear or branched acyl group having 6 to 22 carbon atoms and 0, 1, 2, or 3 double bonds, acyl isethionates with a linear or branched acyl group having 6 to 22 carbon atoms and 0, 1, 2, or 3 double bonds, linear alkane sulfonates having 8 to 24 C atoms, linear alpha-olefin sulfonates having 8 to 24 C atoms, alpha-sulfo fatty acid methyl esters of fatty acids having 8 to 30 C atoms, alkyl sulfates and alkyl polyglycol ether sulfates of the formula R—O($CH_2$—$CH_2O$)$_z$—$SO_3X$, in which R is a preferably linear alkyl group having 8 to 30 C atoms, particularly preferably having 8 to 18 C atoms, z=0 or 1 to 12, particularly preferably 3, and X is a sodium, potassium, magnesium, zinc, ammonium, or a mono-alkanol, dialkanol, or trialkanol ammonium ion having 2 to 4 carbon atoms in the alkanol group, a particularly preferred example being zinc cocoyl ether sulfate with an ethoxylation degree of z=3, mixtures of surface-active hydroxysulfonates according to DE-A-37 25 030, sulfated hydroxyalkyl polyethylene and/or hydroxyalkylene propylene glycol ethers according to DE 3723354, sulfonates of unsaturated fatty acids having 8 to 24 C atoms and 1 to 6 double bonds according to DE 3926344, alkyl and/or alkenyl ether phosphates of the formula (IV),

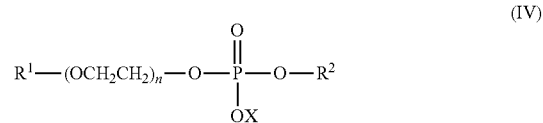

in which $R^1$ preferably stands for an aliphatic hydrocarbon group having 8 to 30 carbon atoms, $R^2$ for hydrogen, a group ($CH_2CH_2O$)$_n R^1$, or X, n for numbers from 1 to 10, and X for hydrogen, an alkali metal or alkaline earth metal or $NR^3R^4R^5R^6$, where $R^3$ to $R^6$ independently of one another stand for a $C_1$ to $C_4$ hydrocarbon group, sulfated fatty acid alkylene glycol esters of the formula $R^7CO(AlkO)_n SO_3M$, in which $R^7CO$ stands for a linear or branched, aliphatic, saturated and/or unsaturated acyl group having 6 to 22 C atoms, Alk stands for $CH_2CH_2$, $CHCH_3CH_2$, and/or $CH_2CHCH_3$, n stands for numbers from 0.5 to 5, and M stands for a cation, as they are described in DE 9736906, monoglyceride sulfates and monoglyceride ether sulfates of the formula (V),

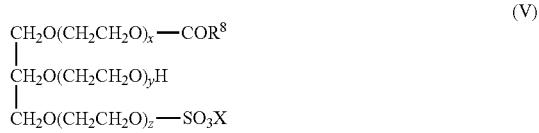

(V)

in which $R^8CO$ stands for a linear or branched acyl group having 6 to 22 carbon atoms, x, y and z in total for 0 or for numbers from 1 to 30, preferably 2 to 10, and X for an alkali or alkaline earth metal. Typical examples of monoglyceride (ether) sulfates suitable in the context of the invention are the reaction products of lauric acid monoglyceride, coconut fatty acid monoglyceride, palmitic acid monoglyceride, stearic acid monoglyceride, oleic acid monoglyceride, and tallow fatty acid monoglyceride, as well as the ethylene oxide adducts thereof to sulfur trioxide or chlorosulfonic acid in the form of their sodium salts. Preferably, monoglyceride sulfates of the formula (V) are used in which $R^8CO$ stands for a linear acyl group having 8 to 18 carbon atoms.

All cationic surface-active substances, suitable for use on the human body or on technical surfaces, are suitable as cationic surfactants in the compositions of the invention.

Cationic surfactants in cosmetic fields of application are characterized in that like amphoteric and zwitterionic surfactants they contribute to a considerably improved cosmetic appearance of the skin and hair. The cationic charge provides for good binding to rather negatively charged surfaces, in particular damaged hair or stressed skin. It is likely again that hydrophobically structured active substances attach increasingly to the long fatty groups of these molecular structures. This causes overall an increased deposition of care substances on the surface of the skin and hair. The hair is more combable, for example, both in the dry and wet state, can be styled more easily, and exhibits a greater shine and a more pleasant feel.

Cationic surfactants are generally derived from ammonium ions and have a structure $(NR^1R^2R^3R^4)^+$ with a correspondingly negatively charged counterion. Cationic ammonium compounds of this type are very well known to the skilled artisan. Other cationic surfactants are, for example, esterquats or imidazolium compounds. Cationic surfactants of the quaternary ammonium compound type, esterquat type, imidazoline type, and amidoamine type can be used particularly preferably according to the invention. Preferred quaternary ammonium compounds are ammonium halides, in particular chlorides and bromides, such as alkyltrimethylammonium chlorides, dialkyldimethylammonium chlorides, and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, and the imidazolium compounds known under the INCI names Quaternium-27 and Quaternium-83. The long alkyl chains of the aforementioned surfactants preferably have 8 to 30 carbon atoms. Typical examples of cationic surfactants are quaternary ammonium compounds and esterquats, particularly quaternized fatty acid trialkanolamine ester salts.

Cationic compounds with behenyl groups, particularly the substances known under the name behentrimonium chloride or bromide (docosanyltrimethylammonium chloride or bromide) can be used particularly preferably according to the invention. Other preferred quaternary ammonium compounds (QAC) have at least two behenyl groups. These substances are available commercially, for example, under the names Genamin® KDMP (Clariant).

Esterquats are known substances that include both at least one ester function and at least one quaternary ammonium group as a structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are marketed, for example, under the trademarks Stepantex®, Dehyquart®, and Armocare®. The products Armocare® VGH-70, an N,N-bis(2-palmitoyloxyethyl)dimethylammonium chloride, and Dehyquart® F-75, Dehyquart® C-4046, Dehyquart® L80, and Dehyquart® AU-35 are examples of such esterquats.

Surface-active compounds, which are suitable use on the human body or on technical surfaces and carry at least one quaternary ammonium group and at least one —COO⁻ or $SO_3^-$ group in the molecule, may be suitable as amphoteric/zwitterionic surfactants. Particularly suitable amphoteric surfactants are the so-called betaines, such as the N-alkyl-N,N-dimethylammonium glycinates, for example, coco alkyl dimethylammonium glycinate and N-acylaminopropyl-N,N-dimethylammonium glycinates, for example, cocoacylaminopropyl dimethylammonium glycinate, and 2-alkyl-3-carboxymethyl-3-hydroxyethyl imidazolines each having 8 to 18 C atoms in the alkyl or acyl group, as well as cocoacylaminoethyl hydroxyethyl carboxymethyl glycinate. A preferred zwitterionic surfactant is the fatty acid amide derivative known under the INCI name of Cocamidopropyl Betaine.

All nonionic surfactants that are suitable for use on the human body or on technical surfaces, for example, but without being limited to these, may also be considered as surface-active compounds that can be used according to the invention:

Nonionic surfactants in the context of the invention are alkoxylates such as polyglycol ethers, fatty alcohol polyglycol ethers, alkyl phenol polyglycol ethers, end-capped polyglycol ether, mixed ethers and hydroxy mixed ethers and fatty acid polyglycol esters. Likewise suitable are block polymers of ethylene oxide and propylene oxide and fatty acid alkanolamides and fatty acid polyglycol ethers. Important classes of nonionic surfactants of the invention are furthermore the amine oxides and the sugar surfactants, in particular alkyl polyglucosides.

Fatty alcohol polyglycol ethers according to the invention are understood to be unbranched or branched, saturated or unsaturated $C_{10-22}$ alcohols, alkoxylated with ethylene (EO) and/or propylene oxide (PO), with a degree of alkoxylation up to 30, preferably ethoxylated $C_{10-18}$ fatty alcohols with an ethoxylation degree of less than 30, preferably with an ethoxylation degree of 1 to 20, in particular of 1 to 12, particularly preferably of 1 to 8, exceedingly preferably of 2 to 5, for example, $C_{12-14}$ fatty alcohol ethoxylates with 2, 3, or 4 EO or a mixture of $C_{12-14}$ fatty alcohol ethoxylates with 3 and 4 EO in a 1 to 1 weight ratio or isotridecyl alcohol ethoxylate with 5, 8, or 12 EO.

Amine oxides

The amine oxides suitable according to the invention include alkylamine oxides, in particular alkyldimethylamine oxides, alkylamidoamine oxides, and alkoxyalkylamine oxides. Preferred amine oxides satisfy the formula VII, $$R^6R^7R^8N^+\text{—}O^{-tm} \quad (VII)$$

$$R^6\text{—}[CO\text{—}NH\text{—}(CH_2)_w]_z\text{—}N+(R^7)(R^8)\text{—}O^- \quad (VII)$$

in which $R^6$ is a saturated or unsaturated $C_{6-22}$ alkyl group, preferably $C_{8-18}$ alkyl group, in particular a saturated $C_{10-16}$ alkyl group, for example, a saturated $C_{12-14}$ alkyl group, which is bound in the alkylamidoamine oxides via a carbonyl amidoalkylene group —CO—NH—$(CH_2)_z$— and in the alkoxyalkylamine oxides via an oxaalkylene group —O—$(CH_2)_z$— to the nitrogen atom N; here z in each case stands for a number from 1 to 10, preferably 2 to 5, in particular 3, $R^7$, $R^8$ independently of one another are a $C_{1-4}$ alkyl group, optionally hydroxyl-substituted such as, e.g., a hydroxyethyl, in particular a methyl group.

Examples of suitable amine oxides are the following compounds according to INCI nomenclature: Almondamidopropylamine Oxide, Babassuamidopropylamine Oxide, Behenamine Oxide, Cocamidopropyl Amine Oxide, Cocamidopropylamine Oxide, Cocamine Oxide, Coco-Morpholine Oxide, Decylamine Oxide, Decyltetradecylamine Oxide, Diaminopyrimidine Oxide, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Hydrogenated Palm Kernel Amine Oxide, Hydrogenated Tallowamine Oxide, Hydroxyethyl Hydroxypropyl C12-15 Alkoxypropylamine Oxide, Isostearamidopropylamine Oxide, Isostearamidopropyl Morpholine Oxide, Lauramidopropylamine Oxide, Lauramine Oxide, Methyl Morpholine Oxide, Milkamidopropyl Amine Oxide, Minkamidopropylamine Oxide, Myristamidopropylamine Oxide, Myristamine Oxide, Myristyl/Cetyl Amine Oxide, Oleamidopropylamine Oxide, Oleamine Oxide, Olivamidopropylamine Oxide, Palmitamidopropylamine Oxide, Palmitamine Oxide, PEG-3 Lauramine Oxide, Potassium Dihydroxyethyl Cocamine Oxide Phosphate, Potassium Trisphosphonomethylamine Oxide, Sesamidopropylamine Oxide, Soyamidopropylamine Oxide, Stearamidopropylamine Oxide, Stearamine Oxide, Tallowamidopropylamine Oxide, Tallowamine Oxide, Undecylenamidopropylamine Oxide und Wheat Germamidopropylamine Oxide. A preferred amine oxide is, for example, Cocamidopropylamine Oxide.

Sugar surfactants

Sugar surfactants are known surface-active compounds which include, for example, the sugar surfactant classes of alkylglucose esters, aldobionamides, gluconamides (sugar acid amides), glycerol amides, glyceroglycolipids, polyhydroxyfatty acid amide sugar surfactants (sugar amides), and alkyl polyglycosides. Sugar surfactants preferred in the context of the teaching of the invention are alkyl polyglycosides and the sugar amides and derivatives thereof, in particular the ethers and esters thereof. The ethers are the products of the reaction of one or more, preferably one, sugar hydroxy group with a compound including one or more hydroxy groups, for example, $C_{1-22}$ alcohols or glycols, such as ethylene and/or propylene glycol; here the sugar hydroxy group can also carry polyethylene glycol and/or polypropylene glycol groups. The esters are the reaction products of one or more, preferably one, sugar hydroxy group with a carboxylic acid, in particular a $C_{6-22}$ fatty acid.

Alkyl polyglycosides

The alkyl polyglycosides (APG) in the context of the teaching of the invention are particularly preferred sugar surfactants and preferably satisfy the general formula $RO(AO)_a[G]_x$, in which R stands for a linear or branched, saturated or unsaturated alkyl group having 6 to 22, preferably 6 to 18, in particular 8 to 16, particularly preferably 8 to 14 carbon atoms, [G] for a glycosidically linked sugar group, and x for a number from 1 to 10, and AO for an alkylene oxy group, e.g., an ethyleneoxy or propyleneoxy group, and "a" for the average degree of alkoxylation of 0 to 20. In this case, the group $(AO)_a$ can also include different alkylene oxy units, e.g., ethyleneoxy or propyleneoxy units, then in the case of a this is the average total degree of alkoxylation, i.e., the sum of the degrees of ethoxylation and propoxylation. Provided not stated differently or in greater detail, the alkyl groups $R^1$ of the APG are linear unsaturated groups with the indicated number of carbon atoms.

APG are nonionic surfactants and represent known substances that can be obtained according to relevant methods of preparative organic chemistry. The subscript x indicates the degree of oligomerization (DP degree), i.e., the distribution of mono- and oligoglycosides, and stands for a number between 1 and 10. Whereas in a given compound x must always be an integer and here can assume primarily the values x=1 to 6, the value of x for a specific alkyl oligoglycoside is an analytically determined mathematical quantity, which is usually a fraction. Preferably, alkyl glycosides with an average degree of oligomerization x of 1.1 to 3.0 are employed. Alkyl glycosides are preferred from the application technology standpoint whose degree of oligomerization is less than 1.7 and is in particular between 1.2 and 1.6. Preferably xylose but in particular glucose is used as the glycosidic sugar.

The alkyl or alkenyl group R is preferably derived from lauryl alcohol, myristyl alcohol, cetyl alcohol, palmoleyl alcohol, stearyl alcohol, isostearyl alcohol, or oleyl alcohol. Furthermore, elaidyl alcohol, petroselinyl alcohol, arachidyl alcohol, gadoleyl alcohol, behenyl alcohol, erucyl alcohol, and technical mixtures thereof can be named.

Particularly preferred APG are not alkoxylated (a=0) and satisfy the formula $RO[G]_x$, in which R as previously stands for a linear or branched, saturated or unsaturated alkyl group having 4 to 22 carbon atoms, [G] for a glycosidically linked sugar group, preferably a glucose group, and x for a number from 1 to 10, preferably 1.1 to 3, in particular 1.2 to 1.6. Accordingly, preferred alkyl polyglycosides are, for example, $C_{8-10}$ and a $C_{12-14}$ alkyl polyglucoside with a DP degree of 1.4 or 1.5, in particular $C_{8-10}$ alkyl-1,5-glucose and $C_{12-14}$ alkyl-1,4-glucose.

In a further embodiment of the invention, the proportion of one or more surfactants, if used, based on the total amount of preparations (A) and/or (B), is 0.5 to 20% by weight, particularly preferably 0.6 to 10% by weight, exceedingly preferably 0.7 to 8% by weight, and in particular 0.8 to 6% by weight, 0.9 to 4% by weight, or 1 to 3% by weight.

Further, the agents of the invention may include other active substances, auxiliary substances, and additives such as, for example, structurants such as glucose, maleic acid, and lactic acid, alkalizing agents such as ammonia, monoethanolamine, potassium hydroxide, and sodium hydroxide; hair-conditioning compounds such as phospholipids, for example, lecithin and kephalins; perfume oils, fiber-structure-improving active substances, particularly mono-, di-, and oligosaccharides such as, for example, glucose, galactose, fructose, fruit sugar, and lactose; dyes for coloring the agent; antidandruff agents such as piroctone olamine, zinc omadine, and climbazole; amino acids and oligopeptides; protein hydrolysates with an animal and/or vegetable base, and in the form of their fatty acid condensation products or optionally anionically or cationically modified derivatives; vegetable oils; light stabilizers and UV blockers; active substances such as panthenol, pantothenic acid, pantolactone, allantoin, pyrrolidinone carboxylic acids, and salts thereof, as well as bisabolol; polyphenols, particularly hydroxycinnamic acids, 6,7-dihydroxycoumarins, hydroxybenzoic acids, catechins, tannins, leukoanthocyanidins, anthocyanidins, flavanones, flavones, and flavonols; ceramides or pseudoceramides; vitamins, provitamins, and vitamin precursors; plant extracts; swelling and penetration agents such as glycerol, propylene glycol monoethyl ethers, carbonates, hydrogen carbonates, guanidines, ureas, and primary, secondary, and tertiary phosphates; opacifiers such as latex, styrene/PVP and styrene/acrylamide copolymers; pearlescent agents such as ethylene glycol mono- and distearate and PEG-3 distearate; pigments and propellants such as propane-butane mixtures, $N_2O$, dimethyl ether, $CO_2$, and air.

The additional active and auxiliary substances are used in the agents of the invention preferably in each case in amounts of 0.0001 to 10% by weight, in particular of 0.0005 to 5% by weight, based on the total weight of dyeing agent (A) or oxidizing agent preparation (B).

The dyeing agents of the invention are preferably produced using a special process, which assures that the solid particles are arranged at the interface between both oil phase and aqueous phase and there form the desired mechanical barrier against the coalescence of the droplets.

A further subject of the present invention is a method for producing a dyeing agent (A) according to the first subject of the invention, comprising the following steps (I) heating (a1) one or more fatty components (F) to a temperature above the melting point of the fatty components (F), (II) adding water (a2), (III) cooling the mixture to a temperature below the melting point of the fatty components (F), (IV) adding (a3) at least one oxidation dye precursor (ODP) and/or at least one direct dye (D), (V) adding (a4) at least one type of microfine particles (P) that have an average particle size of less than 200 μm (micrometers), characterized in that step (V) occurs after step (III).

Particularly preferred is a method of the invention that is characterized by steps (I), followed by step (II), followed by step (III), followed by step (IV), followed by step (V).

Steps (I) to (V) occur particularly preferably with stirring.

The statements made about dyeing agent (A) of the invention and the multi-component packaging unit of the invention apply mutatis mutandis to the preferred embodiments of the method of the invention.

EXAMPLES

1. Dyeing agent (A)

The following dyeing agents were prepared (all quantities are given in % by weight), Shade: black

| Dyeing agent (A) | (AV) comparison | (AE) according to the invention |
|---|---|---|
| Cetearyl alcohol ($C_{16}$-$C_{18}$ fatty alcohols) | 8.0 | 8.0 |
| Lorol techn. ($C_{12}$-$C_{18}$ fatty alcohols) | 2.0 | 2.0 |
| Ceteareth-20 | 0.5 | 0.5 |
| Dehyton K (cocoamidopropyl betaine, 29-32% solution in water) | 2.0 | 2.0 |
| Ceteareth-50 | 1.0 | 1.0 |
| Potassium hydroxide | 0.5 | 0.5 |
| Monoethanolamine | 6.5 | 6.5 |
| Sodium chloride | 0.5 | 0.5 |
| Etidronic acid (1-hydroxyethane-1,1-diphosphonic acid, 60% aqueous solution) | 0.2 | 0.2 |
| Sodium sulfite | 0.2 | 0.2 |
| p-Toluylenediamine, sulfate (x H2SO4) | 3.26 | 3.26 |
| 1,5-Dihydroxynaphthalene | 0.03 | 0.03 |
| Resorcinol | 0.5 | 0.5 |
| 4-Chlororesorcinol | 0.69 | 0.69 |
| 4-Amino-2-hydroxytoluene | 0.03 | 0.03 |
| m-Aminophenol | 0.46 | 0.46 |
| 3-Amino-2-methylamino-6-methoxypyridine | 0.20 | 0.20 |
| Vitamin C (ascorbic acid) | 0.20 | 0.20 |
| Sodium silicate 40/42 (sodium water glass, viscous liquid) | 0.5 | 0.5 |
| Aluminum starch octenylsuccinate, D50 (v) = 16 μm (micrometers) (laser diffractometry) | — | 2.0 |
| Water (dist.) | To 100 | To 100 |

First, the fatty alcohols were melted with stirring to 80° C., and then the surfactants fully dissolved or dispersed in a small portion of water were added. Said mixture was cooled to 45° C. with vigorous stirring. Next, the alkalizing agents, acid, and salts were dissolved in a small amount of water and slowly incorporated into the mixture likewise with constant stirring. After this, all oxidation dye precursors were then predissolved or predispersed in a small amount of water and likewise incorporated into the preparation. The mixture was topped up with water to 95% by weight.

The comparison formulation (AV) was then topped up with water to 100% by weight. The formulation was allowed to cool to room temperature with further stirring.

The finely divided aluminum starch octenylsuccinate was added to the coloring cream of the invention (AE) with stirring and topped up with water to 100% by weight. The formulation was allowed to cool to room temperature with further stirring.

After this, each formulation was filled into a closed vessel.

2. Storage test

Both coloring creams (AV) (comparison) and (AE) (according to the invention) were stored in a closed vessel for 8 weeks at room temperature (22° C.).

| Storage test | (AV) comparison | (AE) according to the invention |
|---|---|---|
| Day of preparation | Emulsion | Emulsion |
| Storage for 1 day, RT | Phase separation (unstable) | Emulsion |

-continued

| Storage test | (AV) comparison | (AE) according to the invention |
|---|---|---|
| Storage for 8 weeks, RT | Phase separation (unstable) | Emulsion |

3. Oxidizing agent preparation (B)

The following oxidizing agent preparation (B) was prepared (all quantities are given in % by weight)

| Oxidizing agent preparation (B) | (B) |
|---|---|
| EDTA (ethylenediaminetetraacetic acid), disodium salt | 0.15 |
| Disodium pyrophosphate | 0.30 |
| Sodium benzoate | 0.04 |
| Cetearyl alcohol | 1.68 |
| PEG-40 Castor Oil | 0.32 |
| Sodium cetearyl sulfate | 0.10 |
| Hydrogen peroxide (50% aqueous solution) | 6.00 |
| Phosphoric acid | 0.04 |
| Water | To 100 |

4. Preparation of the application mixture

After 8 weeks of storage at room temperature, the viscosity of coloring cream (A) and oxidizing agent preparation (B) was measured (22° C./Brookfield viscometer/spindle 5/4 rpm).

Each coloring cream (A) was combined in the quantitative ratio of 1:1 with oxidizing agent preparation (B) (100 g (A) and 100 g (B)), and the application mixture was prepared in this way. The viscosity of the particular application mixture was measured immediately after the preparation (22° C./Brookfield viscometer/spindle 5/4 rpm).

| Viscosity (22° C./Brookfield viscometer/ spindle 5/4 rpm) | (AV) comparison | (AE) according to the invention |
|---|---|---|
| Coloring cream (A) (after 8 weeks of storage) | 35,200 mPas | 22,800 mPas |
| Oxidizing agent preparation (B) (after 8 weeks of storage) | 4600 mPas | 4600 mPas |
| Application mixture ((A) + (B)) (prepared from (A) and (B) after 8 weeks of storage) | 9200 mPas | 12,850 mPas |

The coloring cream (AE) of the invention had a lower viscosity than the comparison formulation (AV). For this reason, (AE) could be mixed better with oxidizing agent preparation (B).

Nevertheless, more viscosity was developed in the application mixture of the invention ((AE) and (B)) than in the application mixture of the comparison ((AV) and (B)). The application mixture of the invention therefore could be applied better to hair and distributed more homogeneously on the head of the subject.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A dyeing agent (A) for dyeing keratinic fibers, in particular human hair, which is present in the form of an oil-in-water emulsion (O/W emulsion), comprising
   (a1) an oil phase, including one or more fatty components (F),
   (a2) an aqueous phase,
   (a3) at least one oxidation dye precursor (ODP) and/or at least one direct dye (D),
   (a4) at least one type of finely divided particles (P) that have an average particle size of less than 200 µm,
   wherein the dyeing agent (A) has a viscosity of 10,000 to 50,000 mPas as measured at 22° C. using a Brookfield viscometer with a spindle 5 at 4 rpm.

2. The dyeing agent (A) according to claim 1, wherein the one or more fatty components (F) are selected from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, and hydrocarbons.

3. The dyeing agent (A) according to claim 1, wherein the one or more fatty components (F) selected from the group consisting of $C_{12}$-$C_{30}$ fatty alcohols in a total amount of 0.5 to 25.0% by weight based on the total weight of the dyeing agent (A).

4. The dyeing agent (A) according to claim 1, wherein the dyeing agent (A), based on its total weight, includes water in an amount of 50.0 to 90.0% by weight.

5. The dyeing agent (A) according to claim 1, wherein the (a3) at least one oxidation dye precursor (ODP) of the developer type is used in the form of its salt and is selected from the group consisting of p-phenylenediamine x$H_2SO_4$, p-phenylenediamine x2 HCl, p-toluylenediamine x$H_2SO_4$, p-toluylenediamine x2 HCl, 2-(2-hydroxyethyl)-p-phenylenediamine x$H_2SO_4$, 2-(2-hydroxyethyl)-p- phenylenediamine x2 HCl, 2-(1,2-dihydroxyethyl)-p-phenylenediamine x$H_2SO_4$, 2-(1,2-dihydroxyethyl)-p-phenylenediamine x2 HCl, N,N-bis(2-hydroxyethyl)-p-phenylenediamine x$H2SO4$, N,N-bis(2-hydroxyethyl)-p-phenylenediaminex2 HCl, 2-methoxymethyl-p-phenylenediaminex$H_2SO_4$, 2-methoxymethyl-p-phenylenediamine x2 HCl, N-(4-amino-3-methylphenyl)-N-[3-(1H-imidazol-1-yl)propyl]amine x$H_2SO_4$, N-(4-amino-3-methylphenyl)-N-[3-(1H-imidazol-1-Apropyl]amine x2 HCl, N-(4-Amino-3-methylphenyl)-N-[3-(1H-imidazol-1-Apropyl]amine x3 HCl, bis(2-hydroxy-5-aminophenyl)methane x$H_2SO_4$, bis(2-hydroxy-5-aminophenyl)methane x2 HCl, 4,5-diamino-1-(2-hydroxyethyl)-1H-pyrazolex$H_2SO_4$, 4,5-diamino-1-(2-hydroxyethyl)-1H-pyrazole x2 HCl, 2,4,5,6-tetraaminopyrimidine x$H_2SO_4$, 2,4,5,6-tetraaminopyrimidine x2 $H_2SO_4$, 2,4,5,6-tetraaminopyrimidine x2 HCl, 2,4,5,6-tetraaminopyrimidine x3 HCl, 2,4,5,6-tetraaminopyrimidine x4 HCl, 4-hydroxy-2,5,6-triaminopyrimidine x$H_2SO_4$, 4-hydroxy-2,5,6-triaminopyrimidine x2 HCl, 2-hydroxy-4,5,6-triaminopyrimidine x$H_2SO_4$, 2-hydroxy-4,5,6-triaminopyrimidine x2 HCl, and 2-hydroxy-4,5,6-triaminopyrimidine x3 HCl.

6. The dyeing agent (A) according to claim 1, wherein the dyeing agent (A), based on the total weight thereof, includes the (a3) one or more oxidation dye precursors (ODP) in a total amount of 2.0 to 8.0% by weight.

7. The dyeing agent (A) according to claim 1, wherein the dyeing agent (A) includes the
(a3) at least one direct dye (D) that carries at least one cationic or at least one anionic charge.

8. The dyeing agent (A) according to claim 1, wherein the dyeing agent (A), based on the total weight of dyeing agent (A), includes the
(a3) one or more direct dyes (D) in a total amount of 2.0 to 8.0% by weight.

9. The dyeing agent (A) according to claim 1, wherein the (a4) at least one type of finely divided particles (P) are finely divided, powdered, optionally coated, and/or optionally modified solids selected from the group consisting of starch, silicon dioxide, iron oxide, titanium oxide, magnesium oxide, aluminum oxide, zinc oxide, calcium aluminate, silicic acid, magnesium silicoaluminate, magnesium metasilicate aluminate, talc, mica, zirconium oxide, colloidal kaolin, bentonite, glass, zinc laurate, microcrystalline cellulose, mother-of-pearl, carbon black, calcium carbonate, and polyalkylsilsesquioxane.

10. The dyeing agent (A) according to claim 9, wherein the (a4) at least one type of finely divided particles (P), are starch and/or silicon dioxide.

11. The dyeing agent (A) according to claim 1, wherein the (a4) at least one type of finely divided particles (P) are selected from the group consisting of finely divided, powdered aluminum starch octenylsuccinate and finely divided, powdered silica dimethyl silylate.

12. The dyeing agent (A) according to claim 1, wherein the (a4) one or more types of finely divided particles (P) are included in a total amount of 0.25 to 15.0% by weight.

13. The dyeing agent (A) according to claim 1, wherein the (a4) at least one type of finely divided particles (P) have an average particle size of 10 nm (nanometers) to 180 µm (micrometers.

14. The dyeing agent (A) according to claim 1, wherein the dyeing agent (A) is substantially free of polymers that are obtained by polymerizing at least one monomer from the group consisting of (meth)acrylic acid, (meth)acrylic acid esters, (meth)acrylamide, ethylene, propylene, styrene, vinylpyrrolidone, and vinyl acetate.

15. A multi-component packaging unit (kit of parts) for the oxidative dyeing of keratinic fibers, in particular human hair, comprising, packaged separately from one another,
a container (I) containing a cosmetic agent (A) and
a container (II) containing a cosmetic agent (B),
wherein
agent (A) in container (I) is a dyeing agent (A) according to claim 1 and
agent (B) in container (II) is an oxidizing agent preparation (B), including hydrogen peroxide,
wherein the oxidizing agent preparation (B) has a viscosity of 1000 to 16,000 mPas as measured at 22° C. using a Brookfield viscometer with a spindle 5 at 4 rpm.

16. The multi-component packaging unit according to claim 15, wherein the mixture of dyeing agent (A) and oxidizing agent preparation (B), when (A) and (B) are mixed in a weight ratio of 1:1, has a viscosity of 10,000 to 50,000 mPas as measured at 22° C. using a Brookfield viscometer with a spindle 5 at 4 rpm.

17. A method for producing a dyeing agent (A) according to claim 1, comprising:
(I) heating (a1) one or more fatty components (F) to a temperature above the melting point of the fatty components (F),
(II) adding water (a2),
(III) cooling the mixture to a temperature below the melting point of the fatty components (F),
(IV) adding (a3) at least one oxidation dye precursor (ODP) and/or at least one direct dye (D), and
(V) adding (a4) at least one type of microfine particles (P) that have an average particle size of less than 200 µm,
wherein step (V) occurs after step (III).

* * * * *